(12) United States Patent
Gustafson et al.

(10) Patent No.: US 9,970,936 B2
(45) Date of Patent: May 15, 2018

(54) METHODS AND MATERIALS FOR ASSESSING IMMUNE SYSTEM PROFILES

(71) Applicant: Mayo Foundation for Medical Education and Research, Rochester, MN (US)

(72) Inventors: Michael P. Gustafson, Rochester, MN (US); Allan B. Dietz, Chatfield, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 23 days.

(21) Appl. No.: 14/442,465

(22) PCT Filed: Nov. 12, 2013

(86) PCT No.: PCT/US2013/069573
§ 371 (c)(1),
(2) Date: May 13, 2015

(87) PCT Pub. No.: WO2014/078272
PCT Pub. Date: May 22, 2014

(65) Prior Publication Data
US 2016/0266115 A1 Sep. 15, 2016

Related U.S. Application Data

(60) Provisional application No. 61/725,902, filed on Nov. 13, 2012.

(51) Int. Cl.
*G01N 33/574* (2006.01)
*G01N 33/569* (2006.01)
*A61K 38/20* (2006.01)

(52) U.S. Cl.
CPC ... *G01N 33/56972* (2013.01); *A61K 38/2013* (2013.01); *G01N 2800/24* (2013.01); *G01N 2800/52* (2013.01)

(58) Field of Classification Search
CPC .................. G01N 33/56972; G01N 33/574
USPC .................................. 435/7.1, 7.24
See application file for complete search history.

(56) References Cited

U.S. PATENT DOCUMENTS

| | | |
|---|---|---|
| 6,376,202 B1 | 4/2002 | Davis |
| 2007/0031443 A1 | 2/2007 | Vaishnaw et al. |
| 2008/0057043 A1 | 3/2008 | Naldini et al. |
| 2012/0141514 A1 | 6/2012 | Kuehne et al. |
| 2012/0183575 A1 | 7/2012 | Gabrielsson |
| 2012/0230989 A1 | 9/2012 | Dietz |
| 2012/0276004 A1 | 11/2012 | Epstein et al. |

FOREIGN PATENT DOCUMENTS

WO  WO2012138857  10/2012

OTHER PUBLICATIONS

Gustafson et al., "Immune monitoring using the predictive power of immune profiles," J Immunother Cancer., 1:7, Jun. 27, 2013.
Appay et al., "Immuno-monitoring of CD8+ T cells in whole blood versus PBMC samples," *J. Immunol. Methods.*, 309(1-2):192-199, Feb. 2006.
Asadullah et al., "Immunodepression following neurosurgical procedures," *Crit Care Med.*, 23(12):1976-1983, Dec. 1995.
Asadullah et al., "Very low monocytic HLA-DR expression indicates high risk of infection—immunomonitoring for patients after neurosurgery and patients during high dose steroid therapy," *Eur J Emerg Med.*, 2(4):184-190, Dec. 1995.
Atzpodien et al., "Adjuvant treatment with interleukin-2- and interferon-alpha2a-based chemoimmunotherapy in renal cell carcinoma post tumour nephrectomy: results of a prospectively randomised trial of the German Cooperative Renal Carcinoma Chemoimmunotherapy Group (DGCIN)," *Br J Cancer.*, 92(5):843-846, Mar. 14, 2005.
Autissier et al., "Evaluation of a 12-color flow cytometry panel to study lymphocyte, monocyte, and dendritic cell subsets in humans," *Cytometry A.*, 77(5):410-419, May 2010.
Axtelle and Pribble, "IC14, a CD14 specific monoclonal antibody, is a potential treatment for patients with severe sepsis," *J Endotoxin Res.*, 7(4):310-314, 2001.
Banham, "Cell-surface IL-7 receptor expression facilitates the purification of FOXP3(+) regulatory T cells," *Trends Immunol.*, 27(12):541-544, Epub Oct. 12, 2006.
Bauer et al., "Accuracy of waste blood measurement in critically ill patients," *Intensive Care Med.*, 37(4):721-722, Epub Jan. 18, 2011.
Bernard et al., "Report of the American-European consensus conference on ARDS: definitions, mechanisms, relevant outcomes and clinical trial coordination. The Consensus Committee," *Intensive Care Med.*, 20(3):225-232, 1994.
Bernard et al., "The American-European Consensus Conference on ARDS. Definitions, mechanisms, relevant outcomes, and clinical trial coordination," *Am. J. Crit. Care Med.*, 149(3):818-824, Mar. 1994.
Cheville et al., "Comparisons of outcome and prognostic features among histologic subtypes of renal cell carcinoma," *Am. J. Surg. Pathol.*, 27(5):612-624, May 2003.
Chow et al., "Rising incidence of renal cell cancer in the United States," *JAMA*, 281(17):1628-1631, May 1999.
Contal and O'Quigley, "An application of changepoint methods in studying the effect of age on survival in breast cancer," *Comput Stat Data Analysis.*, 30(3):253-270, May 28, 1999.
Davis, "A prescription for human immunology," *Immunity*, 29(6):835-838, Dec. 19, 2008.
de Jager et al., "Prerequisites for cytokine measurements in clinical trials with multiplex immunoassays," *BMC Immunol.*, 10:52, Sep. 28, 2009.

(Continued)

*Primary Examiner* — Yan Xiao
(74) *Attorney, Agent, or Firm* — Fish & Richardson P.C.

(57) ABSTRACT

This document provides methods and materials involved in assessing immune system profiles. For example, methods and materials for performing flow cytometry to determine the number of CD4$^+$ lymphocytes, CD8$^+$ lymphocytes, regulatory T cells, B cells, NK cells, granulocytes, CD14$^+$ HLA-DR$^{lo/neg}$ monocytes, and/or CD86$^+$ monocytes per unit volume (e.g., cells per μL or mL) of whole blood (e.g., fresh, un-manipulated whole blood) obtained from a mammal (e.g., a human) are provided.

3 Claims, 23 Drawing Sheets

(56) References Cited

OTHER PUBLICATIONS

Deininger et al., "Expression and release of CD14 in astrocytic brain tumors," *Acta Neuropathol.*, 106(3):271-277, Epub Jun. 27, 2003.
Diaz-Montero et al., "Increased circulating myeloid-derived suppressor cells correlate with clinical cancer stage, metastatic tumor burden, and doxorubicin-cyclophosphamide chemotherapy," *Cancer Immunol Immunother.*, 58(1):49-59, print Jan. 2009, Epub Apr. 2008.
Ege et al., "Prediction of survival using absolute lymphocyte count for newly diagnosed patients with multiple myeloma: a retrospective study," *Br J Haematol*, 141(6):792-798, Jun. 2008.
Filipazzi et al., "Identification of a new subset of myeloid suppressor cells in peripheral blood of melanoma patients with modulation by a granulocyte-macrophage colony-stimulation factor-based antitumor vaccine," *J Clin Oncol.*, 25(18):2546-2553, Jun. 2007.
Gabrilovich and Nagaraj, "Myeloid-derived suppressor cells as regulators of the immune system," *Nat Rev Immunol.*, 9(3):162-174, Mar. 2009.
Gettman et al., "Pathologic staging of renal cell carcinoma: significance of tumor classification with the 1997 TNM staging system," *Cancer*, 91:354-361, Jan. 2001.
Gustafson et al., "Association of an increased frequency of CD14+ HLA-DR lo/neg monocytes with decreased time to progression in chronic lymphocytic leukaemia (CLL)," *Br J Haematol.*, 156(5):674-676, Epub Nov. 3, 2011.
Gustafson et al., "Systemic immune suppression in glioblastoma: the interplay between CD14+HLA-DRlo/neg monocytes, tumor factors, and dexamethasone," *Neuro Oncol.*, 12(7):631-644, Epub Feb. 23, 2010.
Harton and Ting, "Class II transactivator: mastering the art of major histocompatibility complex expression," *Mol Cell Biol.*, 20(17):6185-6194, Sep. 2000.
Hoechst et al., "A new population of myeloid-derived suppressor cells in hepatocellular carcinoma patients induces CD4(+)CD25(+)Foxp3(+) T cells," *Gastroenterology*, 135(1):234-243, print Jul. 2008 Epub Mar. 2008.
Höflich et al., "Regulatory immunodeficiency and monocyte deactivation Assessment based on HLA-DR expression," *Clinical and Applied Immunology Reviews*, 2(6):337-344, Oct.-Dec. 2002.
Iscimen et al., Risk factors for the development of acute lung injury in patients with septic shock: an observational cohort study, *Crit Care Med.*, 36(5):1518-1522, May 2008.
Iwakami et al., "Granulocyte and monocyte adsorption apheresis therapy modulates monocyte-derived dendritic cell function in patients with ulcerative colitis," *Ther Apher Dial.*, 13(2):138-146, Apr. 2009.
Kiertscher et al., "Tumors promote altered maturation and early apoptosis of monocyte-derived dendritic cells," *J Immunol.*, 164(3):1269-1276, Feb. 2000.
Ko et al., "Sunitinib mediates reversal of myeloid-derived suppressor cell accumulation in renal cell carcinoma patients," *Clin Cancer Res.*, 15(6):2148-2157, Epub Mar. 10, 2009.
Kohrt et al., "Profile of immune cells in axillary lymph nodes predicts disease-free survival in breast cancer," *PLoS Med.*, 2(9):e284, Epub Sep. 6, 2005.
Lin et al "Immunosuppressive CD14+HLA-DR(low)/- monocytes in B-cell non-Hodgkin lymphoma," *Blood* 117(3):872-881, Jan. 20, 2011, Epub Nov. 9, 2010.
Longo et al., "Single-cell network profiling of peripheral blood mononuclear cells from healthy donors reveals age- and race-associated differences in immune signaling pathway activation," *J Immunol.*, 188(4):1717-1725, Epub. Jan. 13, 2012.
Maas et al., "Immune profiles of pediatric cancer patients," presented at the Society for Immunotherapy of Cancer 2011 Annual Meeting, Nov. 4-6, 2011, 1 page.
Mayo Clinic, ClinicalTrials.gov Identifier: NCT00562328, "Rituximab, Alemtuzumab, and GM-CSF As First-Line Therapy in Treating Patients With Early-Stage Chronic Lymphocytic Leukemia," ClinicalTrials.gov [online] Nov. 21, 2007 [retrieved Oct. 28, 2015]. Retrieved from the Internet: <URL: https://www.clinicaltrials.gov/ct2/show/NCT00562328?term=NCT00562328&rank=1>, 5 pages.
Minniti et al., "Phase II study of short-course radiotherapy plus concomitant and adjuvant temozolomide in elderly patients with glioblastoma," *Int J Radiat Oncol Biol Phys.*, 83(1):93-99, Epub Nov. 11, 2011.
Moore et al., "Postinjury multiple organ failure: a bimodal phenomenon," *J Trauma.*, 40(4):501-510; discussion 510-512, Apr. 1996.
Morimura et al., "Monocyte subpopulations in human gliomas: expression of Fc and complement receptors and correlation with tumor proliferation," *Acta Neuropathol.*, 80(3):287-294, 1990.
Ostrand-Rosenberg and Sinha, "Myeloid-derived suppressor cells: linking inflammation and cancer," *J Immunol.*, 182(8):4499-506, Apr. 2009.
Palmer et al., "Cell-type specific gene expression profiles of leukocytes in human peripheral blood," *BMC Genomics*, 7:115, May 16, 2006.
Peters et al., "Acquired immunoparalysis in paediatric intensive care: prospective observational study," *BMJ.*, 319(7210):609-610, Sep. 1999.
Porrata et al., "Early lymphocyte recovery predicts superior survival after autologous stem cell transplantation in non-Hodgkin lymphoma: a prospective study," *Biology of Blood & Marrow Transplantation*, 14(7):807-816, Jul. 2008.
Rapp et al., "Cellular immunity of patients with malignant glioma: prerequisites for dendritic cell vaccination immunotherapy," *J Neurosurg.*, 105(1):41-50, Jul. 2006.
Rittirsch et al., "Harmful molecular mechanisms in sepsis," *Nat Rev Immunol.*, 8(10):776-787, Oct. 2008.
Schimke et al., "Anti-CD14 mAb treatment provides therapeutic benefit after in vivo exposure to endotoxin," *Proc Natl Acad Sci U S A.*, 95(23):13875-13880, Nov. 1998.
Serafini et al., "Myeloid-derived suppressor cells promote cross-tolerance in B-cell lymphoma by expanding regulatory T cells," *Cancer Res.*, 68(13):5439-5449, Jul. 2008.
Serafini et al., "Phosphodiesterase-5 inhibition augments endogenous antitumor immunity by reducing myeloid-derived suppressor cell function," *J Exp Med.*, 203(12):2691-2702, Nov. 2006.
Sester et al., "Strong depletion of CD14(+)CD16(+) monocytes during haemodialysis treatment," *Nephrol Dial Transplant.*, 16(7):1402-1408, Jul. 2001.
Sinha et al., "Proinflammatory S100 proteins regulate the accumulation of myeloid-derived suppressor cells," *J Immunol.*, 181(7):4666-4675, Oct. 2008.
Soini et al., "Treatment of follicular non-Hodgkin's lymphoma with or without rituximab: cost-effectiveness and value of information based on a 5-year follow-up," *Ann Oncol.*, 22(5):1189-1197, Epub Dec. 6, 2010.
Takeda et al., "MHC class II molecules are not required for survival of newly generated CD4+ T cells, but affect their long-term life span," *Immunity*, 5(3):217-228, Sep. 1996.
Tokunaga et al., "Successful treatment of renal cell carcinoma with mediastinal lymph node metastasis by interleukin-2: a case report," *Tokai J Exp Clin Med.*, 30(2):111-115, Jul. 2005.
van Ravenswaay Claasen, "Tumor infiltrating cells in human cancer. On the possible role of CD16+ macrophages in antitumor cytotoxicity," *Lab Invest.*, 67(2):166-174, Aug. 1992.
Viret and Janeway, "MHC and T cell development," *Rev Immunogenet.*, 1(1):91-104, 1999.
Vuk-Pavlovic et al., "Rebuilding immunity in cancer patients," *Blood Cells Mol Dis.*, 40(1):94-100, print Jan.-Feb. 2008, Epub Sep. 2007.
Webster et al., "Mononuclear cell infiltration in clear-cell renal cell carcinoma independently predicts patient survival," *Cancer*, 107(1):46-53, Jul. 1, 2006.
Xin et al., "Sunitinib inhibition of Stat3 induces renal cell carcinoma tumor cell apoptosis and reduces immunosuppressive cells," *Cancer Res.*, 69(6):2506-2513, print Mar. 2009, Epub Feb. 2009.

(56) References Cited

OTHER PUBLICATIONS

Yu et al., [A study on HLA-Dr expression of brain tumor cells and mononuclear cell subsets infiltrating in these tumors], [Article in Chinese], Zhonghua Bing Li Xue Za Zhi, 23(4):221-223, Aug. 1994, [English abstract only].
Zea et al., "Arginase-producing myeloid suppressor cells in renal cell carcinoma patients: a mechanism of tumor evasion," *Cancer Res.*, 65(8):3044-3048, Apr. 2005.
International Preliminary Report on Patentability for Application No. PCT/US2011/058981, dated May 7, 2013, 4 pages.
International Preliminary Report on Patentability for PCT/US2010/055856, dated May 15, 2012, 5 pages.
International Preliminary Report on Patentability for PCT/US2013/069573, dated May 28, 2015, 13 pages.
International Preliminary Report on Patentability for PCT/US2014/037058, dated Nov. 19, 2015, 6 pages.
International Search Report and Written Opinion for Application No. PCT/US2011/058981, dated Apr. 27, 2012, 5 pages.
International Search Report and Written Opinion for PCT/US2010/055856, dated Aug. 1, 2011, 6 pages.
International Search Report and Written Opinion for PCT/US2013/069573, dated Feb. 27, 2014, 9 pages.
International Search Report and Written Opinion for PCT/US2014/37058, dated Sep. 29, 2014, 7 pages.

| Cohort | Total | HV | GBM | NHL | RCC | OVA | ALL |
|---|---|---|---|---|---|---|---|
| Profile 1 | 87 | 33 | 9 | 14 | 16 | 13 | 2 |
| Profile 2 | 13 | 7 | 3 | 2 | 0 | 1 | 0 |
| Profile 3 | 15 | 0 | 3 | 0 | 7 | 0 | 5 |
| Profile 4 | 26 | 0 | 10 | 3 | 2 | 2 | 9 |
| Profile 5 | 16 | 0 | 1 | 8 | 0 | 1 | 6 |
| None | 3 | 0 | 1 | 1 | 0 | 0 | 1 |
| Totals | 160 | 40 | 27 | 28 | 25 | 17 | 23 |

FIG. 3B

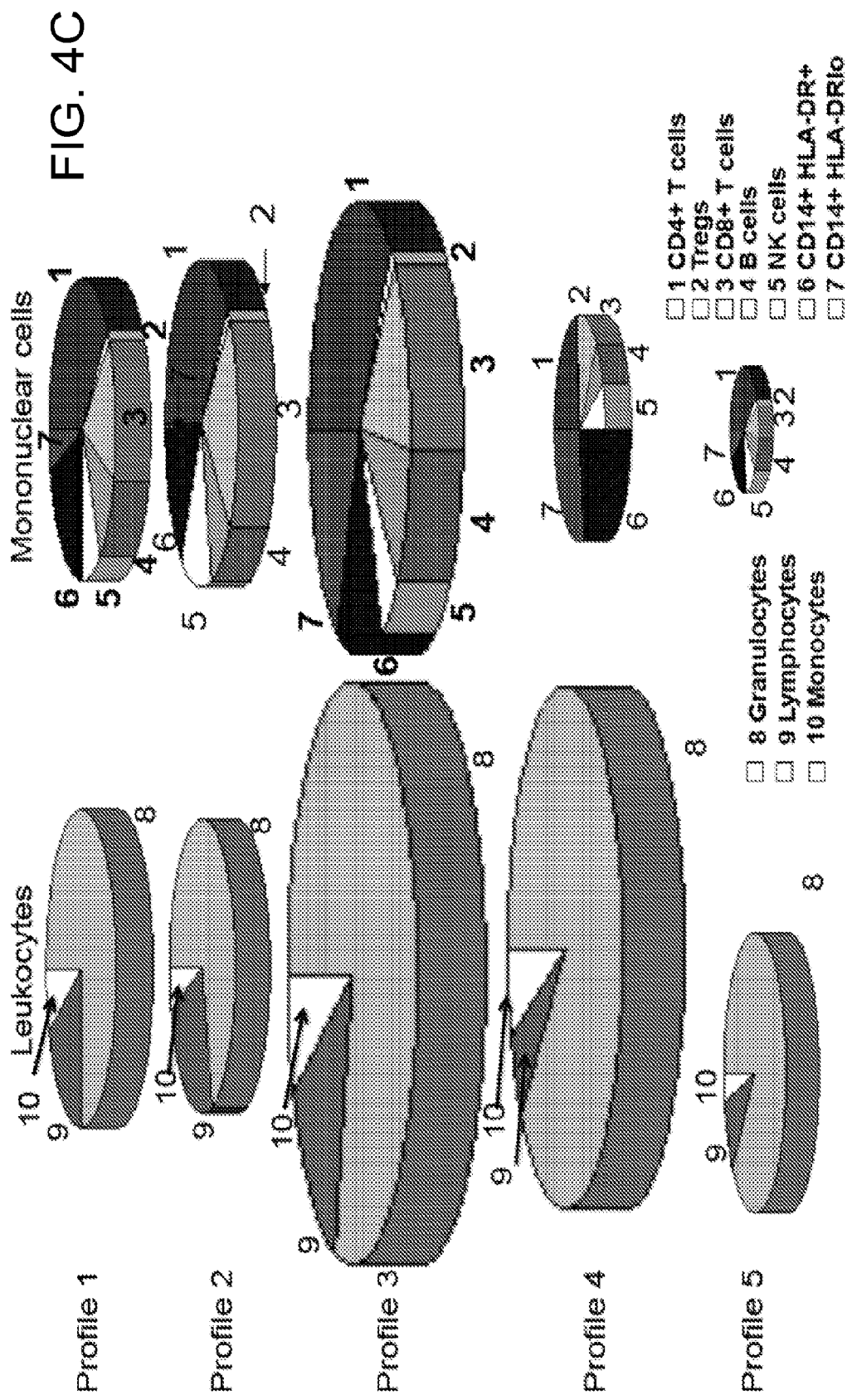

BeckmanCoulter Immunophenotyping Panels

Lyse No Wash w/ FlowCount Panel

| Protocol | FITC | PE | ECD | PC5.5 | PC7 | APC | APC-700 | APC-750 | Pac Blu | KrO |
|---|---|---|---|---|---|---|---|---|---|---|
| Verify | CD8 10 ul | CD2 10 | CD20 10 | CD14 3 | CD3 3 | CD7 3 | CD19 2 | CD5 5 | CD4 5 | CD45 5 |
| TBNK+14 | CD15 10 ul | ☒ TCR 10 | CD16 6 | CD14 3 | CD56 5 | CD19 5 | CD8 5 | CD3 5 | CD4 5 | CD45 5 |

Lyse Wash Panel

| Protocol | FITC | PE | ECD | PC5.5 | PC7 | APC | APC-700 | APC-750 | Pac Blu | KrO |
|---|---|---|---|---|---|---|---|---|---|---|
| Verify | CD8 10 ul | CD2 10 | CD20 10 | CD14 3 | CD3 3 | CD7 3 | CD19 2 | CD5 5 | CD4 5 | CD45 5 |
| CD4 Treg/Memory/Naive | CCR7 20 ul ICOS | CD27 20 | CD45RO 10 | CD25 10 | CD69 10 CCR7 | CD62L 20 | CD127 10 | CD45RA 10 | CD4 5 | CD3 10 |
| CD8 Memory/Naive | CCR7 20 ul ICOS | CD27 20 | CD45RO 10 | CD25 10 | CD69 10 CCR7 | CD62L 20 | CD8 5 | CD45RA 10 | HLA-DR 5 | CD3 10 |
| T cell signaling | CD154 (CD40L) 20 ul | CD272 (BTLA) 10 | CD8 5 | TIM-3 10 | PD-1 10 | CD152 (CTLA4) 20 | | CD28 10 | CD4 5 | CD3 10 |
| B cell | IgD 20 ul | CD27 20 | CD20 10 | CD38 10 | CD5 5 | IgM 5 | CD19 2 | CD24 10 | CD21 10 | CD45 5 |

Each box represents the antibody with the volume of antibody required underneath.

FIG. 9

| Protocol | FITC | PE | ECD | PC5.5 | PC7 | APC | APC-700 | APC-750 | Pac Blu | KrO |
|---|---|---|---|---|---|---|---|---|---|---|
| Classical /non monos | CD80 20 | TF (CD142) 20 | CD14 5 | | CD64 10 | CD86 20 | | CD16 10 | HLA-DR 10 | CD45 5 |
| Grans | CD66b 20 | CD63 20 | CD14 5 | CD44 5 | CD203c 10 | CCR3 20 | CD16 3 | CD49d 10 | CD15 10 | CD45 5 |
| MDSCs | Lineage 20 | B7-H1 10 | | | PD-1 10 | CD33 10 | | | HLA-DR 10 | CD45 5 |
| Mono signaling | TNFRII 20 | CD115 10 | CD14 5 | | CD11b 5 | CD40 20 | | CD16 10 | HLA-DR 10 | CD45 5 |

Eosinophils: CD16-/CD15+; activation markers CD44, CD66b
Basophils: CCR3+; activation markers CD63 and CD203c Non-Beckman Reagents (lymphocytes)
CCR7 FITC R&D Systems
CD62L APC BD
TIM-3 APC eBioscience
CD154FITC BD
HLA-DR PerCP BD
CD272 APC Biolegend
CD152 (CTLA4) BD

FIG. 9 (CONT)

Non-Beckman Reagents (monocytes)
CD44 Percp 5.5 BD
CCR3 APC R&D
TNFRII FITC R&D Systems
B7-H1 PE      eBioscience
CD115 PE     BD
Lineage FITC BD
CD142 PE     BD
CD86 APC BD 555660
CD40 APC BD 555591

Possible Treg protocol

| Protocol | FITC | PE | ECD | PC5.5 | PC7 | APC | APC-700 | APC-750 | Pac Blu | KrO |
|---|---|---|---|---|---|---|---|---|---|---|
| Treg | CD25 | BTLA | CD8 | TIM-3 | PD-1 | CD152 | CD127 | CD28 | CD4 | CD3 |

For CD4 and CD8 tubes, ICOS-FITC can be replaced with CCR7, Add CCR7 PC-7 for CD69

FIG. 9 (CONT)

METHODS AND MATERIALS FOR ASSESSING IMMUNE SYSTEM PROFILES

CROSS-REFERENCE TO RELATED APPLICATION

This application is a National Stage application under 35 U.S.C. § 371 of International Application No. PCT/US2013/069573, having and International Filing Date of Nov. 12, 2013, which claims the benefit of U.S. Provisional Application Ser. No. 61/725,902, filed Nov. 13, 2012. The disclosure of the prior applications are considered part of (and are incorporated by reference in) the disclosure of this application.

BACKGROUND

1. Technical Field

This document relates to methods and materials involved in assessing immune system profiles. For example, this document provides methods and materials for performing flow cytometry to determine the immune status of a mammal (e.g., a human) using whole blood (e.g., fresh, un-manipulated whole blood) obtained from the mammal.

2. Background Information

The immune system of a mammal is a system of biological structures and processes that helps protect the mammal from diseases by identifying and killing pathogens and tumor cells. It also plays a role in an organism's homeostasis and in tissue healing and repair. The immune system is made up of a combination of white blood cells (leukocytes) transported through the body by blood. A monocyte is one type of white blood cell that is part of the immune system. Monocytes can have several roles in the immune system. For example, monocytes can migrate to sites of infection and differentiate into macrophages and dendritic cells. Another type of cell that is part of the immune system is a CD4$^+$ T cell. CD4$^+$ T cells are a sub-group of lymphocytes that help activate and direct other cells of the immune system.

SUMMARY

This document provides methods and materials involved in assessing immune system profiles. For example, this document provides methods and materials for performing flow cytometry to determine the immune status of a mammal (e.g., a human) using whole blood (e.g., fresh, un-manipulated whole blood) obtained from the mammal.

In some cases, the immune status of a mammal is determined by measuring, for example, the number of CD4$^+$ lymphocytes, CD8$^+$ lymphocytes, regulatory T cells, B cells, NK cells, granulocytes, CD14$^+$HLA-DR$^{lo/neg}$ monocytes, and/or CD86$^+$ monocytes per unit volume (e.g., cells per µL or mL). The immune status can be determined by quantitating representatives of each major category of leukocytes (e.g., granulocytes, NK cells, T cells, B cells, myeloid, lymphocytes etc.) and comparing the amount and distribution of these cells to the numbers found in a database of similar measurements from a population of individuals. The comparison to this database can be used to classify the mammal as having a particular immune system profile (e.g., immune system profile 1, immune system profile 2, immune system profile 3, immune system profile 4, or immune system profile 5). Immune system profiles can be used to identify appropriate therapies for different pathologies.

In some cases, a method provided herein for determining the immune status of a mammal can include three steps. First, the measurement of leukocyte subtypes in a manner that allows the number of cells per unit volume such as the number of a subtype per µL of blood volume can be determined. This can be an individual immune phenotype. Second, a collection of a sufficient number of individual immune phenotypes that are together within a mammal can be used to generate a database. The database can then be analyzed to segregate like immune phenotypes using an analysis tool that can perform similarity analyses (e.g., hierarchical clustering or PCA analysis). Clusters of immune phenotypes can be considered immune profiles. Third, once the immune profiles are characterized, an individual immune phenotype can be compared to the database to identify the underlying profile that individual belongs to. Immune profiles can be used to predict response to therapy, identify subtypes that correlate (or inversely correlate), or diagnose pathological subtypes.

In some cases, this document provides methods and materials for performing flow cytometry to determine an immune phenotype that includes the number of CD4$^+$ lymphocytes, CD8$^+$ lymphocytes, regulatory T cells, B cells, NK cells, granulocytes, CD14$^+$HLA-DR$^{lo/neg}$ monocytes, and/or CD86$^+$ monocytes per unit volume (e.g., cells per µL or mL) of whole blood (e.g., fresh, un-manipulated whole blood) obtained from a mammal (e.g., a human). The numbers of such cells per unit volume can be compared to immune profile reference information within a database obtained from similarly screened controls. Based at least in part on the comparison information within the database, the mammal can be identified as having a particular immune system profile (e.g., immune system profile 1, immune system profile 2, immune system profile 3, immune system profile 4, or immune system profile 5).

As described herein, fresh, un-manipulated whole blood obtained from a mammal (e.g., a human) can be assessed using flow cytometry to determine the number of one or more (e.g., two, three, four, five, six, seven, or eight) of the following cell types per unit volume (e.g., µL): CD4$^+$ lymphocytes, CD8$^+$ lymphocytes, regulatory T cells, B cells, NK cells, granulocytes, CD14$^+$HLA-DR$^{lo/neg}$ monocytes, and CD86$^+$ monocytes. For example, fresh, un-manipulated whole blood obtained from a human can be assessed using flow cytometry to determine the number CD4$^+$ lymphocytes, CD8$^+$ lymphocytes, regulatory T cells, B cells, NK cells, granulocytes, CD14$^+$HLA-DR$^{lo/neg}$ monocytes, and CD86$^+$ monocytes per µL. Such cell numbers can be used to classify the mammal as having a particular immune system profile (e.g., immune system profile 1, immune system profile 2, immune system profile 3, immune system profile 4, or immune system profile 5) by, for example, identifying individuals whose immune systems cluster together. Mammals having immune system profile 1 or 2 can be healthy or can be likely to have a favorable medical outcome for a particular medical condition (e.g., cancer, autoimmunity, sepsis, wound healing, or infection). Mammals having other immune system profiles (e.g., immune system profiles 3, 4, or 5) can be likely to have a poorer medical outcome for a particular medical condition (e.g., cancer, sepsis, autoimmunity, wound healing, or infection). The methods and material provided herein can be used to identify immune profiles that may react consistently within a profile even in the presence of a different underlying pathology. Thus, immune modulating therapies can be tested on each immune profile, and the results logically extended to other immune profiles. The ability to identify the medical outcome as described herein can be related to the size of the comparative database. Sufficient database size can allow differential outcomes to be determined for each individual profile.

The methods and materials provided herein can allow clinicians to provide patients with information about the state of their immune system and likely outcomes for various medical conditions. In some cases, such information can allow clinicians and patients to determine proper treatment options. For example, the methods and materials provided herein can be used to develop or select appropriate treatments for cancer patients.

In general, one aspect of this document features a method for treating a human having glioblastoma. The method comprises, or consists essentially of, (a) performing flow cytometry using a blood sample obtained from a human having glioblastoma to identify the human as having an immune system profile of a population of healthy humans, and (b) administering surgery, radiation, or chemotherapy to the human. The method can comprise performing flow cytometry using the blood sample to identify the human as having the immune system profile.

In another aspect, this document features a method for treating a human having renal cell carcinoma. The method comprises, or consists essentially of, (a) performing flow cytometry using a blood sample obtained from a human having renal cell carcinoma to identify the human as having an immune system profile of a population of healthy humans, and (b) administering surgery, IL-2, or cryotherapy to the human. The method can comprise performing flow cytometry using the blood sample to identify the human as having the immune system profile.

In another aspect, this document features a method for treating a human having non-Hodgkin lymphoma, wherein the method comprises, or consists essentially of, (a) performing flow cytometry using a blood sample obtained from a human having non-Hodgkin lymphoma to identify the human as having an immune system profile of a population of healthy humans, and (b) administering CHOP, RCHOP, or radiotherapy to the human. The method can comprise performing flow cytometry using the blood sample to identify the human as having the immune system profile.

In another aspect, this document features a method for determining the immune system profile of a human, wherein the method comprises, or consists essentially of, (a) performing flow cytometry using whole blood obtained from a human to determine the numbers of $CD4^+$ lymphocytes, $CD8^+$ lymphocytes, regulatory T cells, B cells, NK cells, granulocytes, $CD14^+HLA-DR^{lo/neg}$ monocytes, and $CD86^+$ monocytes per unit volume of the whole blood, (b) comparing the numbers to information within a database, wherein the database comprises the numbers of CD4 lymphocytes, $CD8^+$ lymphocytes, regulatory T cells, B cells, NK cells, granulocytes, $CD14^+HLA-DR^{lo/neg}$ monocytes, and $CD86^+$ monocytes per unit volume present within a population of healthy humans and a population of humans with a medical condition having a known outcome for the medical condition, and (c) classifying the human as having an immune system profile comparable to that of at least one collection of members within the database. The human can be classified as having immune system profile of a population of healthy humans. The whole blood can be a fresh, un-manipulated whole blood sample obtained from the human.

In another aspect, this document features a method for assessing the likelihood that a mammal having a medical condition will experience a favorable or unfavorable outcome, wherein the method comprises, or consists essentially of, (a) performing flow cytometry to determine if a whole blood obtained from a human contains a $CD4^+/CD14^+HLA-DR^{lo/neg}$ ratio greater than or less than 2, (b) classifying the mammal as being likely to experience a favorable outcome of the medical condition if the whole blood contains a $CD4^+/CD14^+HLA-DR^{lo/neg}$ ratio greater than 2, and (c) classifying the mammal as being likely to experience an unfavorable outcome of the medical condition if the whole blood contains a $CD4^+/CD14^+HLA-DR^{lo/neg}$ ratio less than 2. The mammal can be a human. The medical condition can be cancer. The cancer can be glioblastoma. The whole blood can contain a $CD4^+/CD14^+HLA-DR^{lo/neg}$ ratio greater than 2, and wherein the method can comprise classifying the mammal as being likely to experience a favorable outcome. The favorable outcome can comprise surviving the glioblastoma for more than 600 days. The whole blood can contain a $CD4^+/CD14^+HLA-DR^{lo/neg}$ ratio less than 2, and wherein the method can comprise classifying the mammal as being likely to experience an unfavorable outcome. The unfavorable outcome can comprise surviving the glioblastoma for less than 400 days. The cancer can be a lymphoma. The whole blood can contain a $CD4^+/CD14^+HLA-DR^{lo/neg}$ ratio greater than 2, and wherein the method can comprise classifying the mammal as being likely to experience a favorable outcome. The favorable outcome can comprise surviving the lymphoma for greater than 750 days. The whole blood can contain a $CD4^+/CD14^+HLA-DR^{lo/neg}$ ratio less than 2, and wherein the method can comprise classifying the mammal as being likely to experience an unfavorable outcome. The unfavorable outcome can comprise a likelihood of not surviving the lymphoma for greater than 750 days.

In another aspect, this document features the use of an immune profile to speed test immune modulating drugs by testing drugs based on patients with the same profile and using that to treat other patients with the same profile but a different underlying pathology.

In another aspect, this document features the use of an immune profile to determine when to stop dosing for immune modulating drugs. In some cases, a drug can continue to be dosed to solicit a change in an immune profile until the profile changes to that of a healthy individual.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 2A contains the clustering of patients with glioblastoma (GBM; n=27). GBM patients were further identified based on the presences of pre-operative dexamethasone (a known immune suppressor) or its absence. The results of the clustering are included in tabular form demonstrating the relationship between the identified profile and the underlying disease. FIG. 2B contains the clustering of patients with non-Hodgkin lymphoma (NHL; n=28). The tabular results from the clustering are included showing the number of healthy volunteers and NHL patients in each of the profiles. FIG. 2C contains the clustering of renal cell carcinoma patients (RCC; n=25). The tabular results from the clustering are included showing the number of healthy volunteers and RCC patients in each of the profiles. FIG. 2D contains the clustering of ovarian cancer patients (OVA; n=17). The tabular results from the clustering are included showing the number of healthy volunteers and OVA patients in each of the profiles. FIG. 2E contains the clustering of patients with acute lung injury with or at risk for sepsis (ALI; n=23). ALI patients were further identified as those with or without confirmed sepsis as well as those that did or did not survive the episode. The tabular results from the clustering are included showing the number of healthy volunteers and ALI (with and without sepsis) patients in each of the profiles.

FIGS. 3A and 3B contains data of distinct immune profiles that are shared across patient populations. Ten immune markers for each individual from healthy volunteers (n=40) and patients (n=120) were used as sample data for combined clustering analysis. FIG. 3A is a hierarchical clustering dendrogram of patients and HV. Profiles were assigned based on the separation of the clustering trees. FIG. 3B is a tabular representation of the demographics of the patients within each profile. The composition of the profile is dependent on the members tested. The profiles determined within a patient specific analysis do not correspond to the profiles identified with the whole group.

FIG. 4A-4C demonstrates that the immune profiles are distinct in relative and absolute composition of immune markers. Immune markers from each subject in a designated profile were evaluated for statistical significance. FIG. 4A contains graphs comparing immune marker cell counts. Box and whisker plots show mean, maximum, and minimum values for each data set. Box represents the 25th to 75th percentile range. HV=healthy volunteers only. *=p<0.05 and **=p<0.0001. Each profile was compared to the healthy volunteer cohort. FIG. 4B contains graphs comparing immune marker percentages. Box and whisker plots show mean, maximum, and minimum values for each data set. Box represents the 25th to 75th percentile range. HV=healthy volunteers only. *=p<0.05 and **=p<0.0001. Each profile was compared to the healthy volunteer cohort. FIG. 4C contains pie graph visualizations of immune profile size and composition. To develop a picture of the composition of circulating populations, selected immune markers (in cells/µL) were totaled, and the means were totaled within a profile. The average profile was used to reconstruct the exemplar within each profile. Graph size represents total leukocytes/µL for the average profile relative to the average of Profile 1. Graphs on the left show the three major components of leukocytes. Graphs on the right show selected proportions of mononuclear cells.

FIG. 8A. An additional 13 immune markers were added to the original ten. Cancer patients (n=48) and healthy volunteers (n=31) in a subset of patients and analyzed as in FIG. 2. White boxes in dendrogram indicate that data was not collected or deemed suitable for analysis. For correlative studies, values from all 160 healthy volunteers and patients were used. FIG. 8B contains data of monocytes or granulocytes plotted against $CD14^+HLA-DR^{lo/neg}$ monocyte cell counts, and CD4 T cell counts plotted against the percentage of $CD14^+ HLA-DR^{lo/neg}$ monocytes of total $CD14^+$ monocytes. P values were calculated using the Spearman non-parametric correlation test. FIG. 8C is a graph plotting overall survival for GBM, NHL, and RCC patients adjusted for age and disease. A ratio of cells/µL of CD4 T cell to $CD14^+HLA-DR^{lo/neg}$ monocytes was calculated for each patient and subgrouped into those above or below a cut-off value of 2.0. Patients with ratio at or above 2.0 (similar to healthy volunteers; dashed line) had a median overall survival of 30 months, and those below 2.0 (solid line) had a median overall survival of 9 months.

FIG. 9 contains tables listing examples of immunophenotyping panels that can be used as described herein.

DETAILED DESCRIPTION

Figure 1:
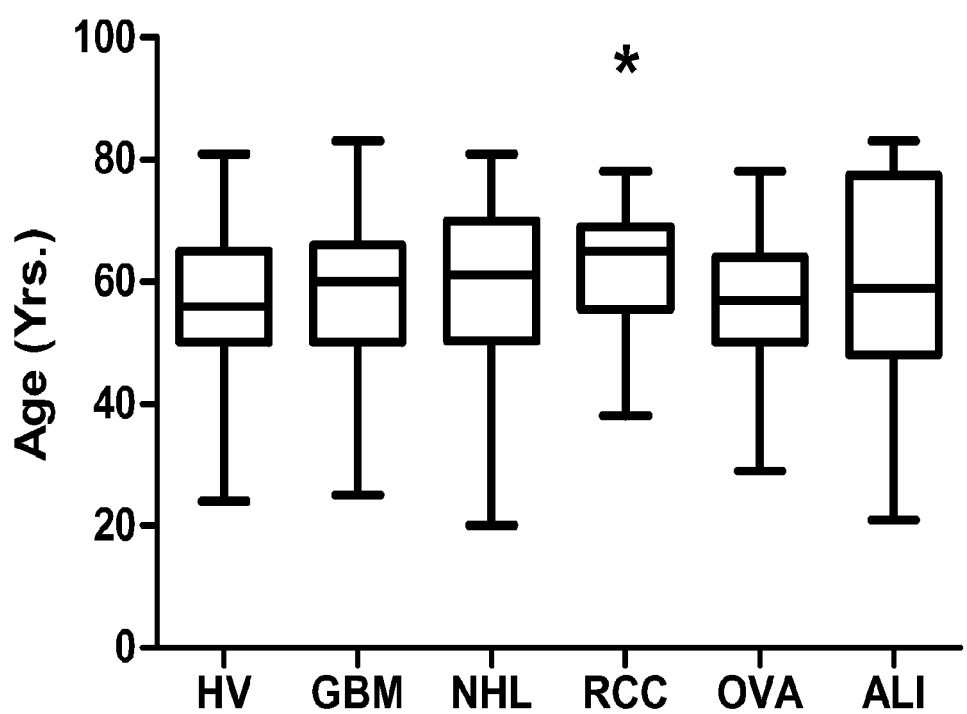
FIG. 1 is graph plotting the age of subjects by disease group. * indicates p value <0.05 as compared to healthy volunteers (HV).

This document provides methods and materials related to assessing immune system profiles. For example, this document provides methods and materials for performing flow cytometry to determine the number of leukocyte subsets in circulation. These subsets can include the number of $CD4^+$ lymphocytes, $CD8^+$ lymphocytes, regulatory T cells, B cells, NK cells, granulocytes, lymphocytes, monocytes, T cells, $CD14^+HLA-DR^{lo/neg}$ monocytes, and/or $CD86^+$ monocytes per unit volume (e.g., cells per µL or mL) of whole blood (e.g., fresh, un-manipulated whole blood) obtained from a mammal (e.g., a human). After generating information about the number of leukocyte subsets within a mammal, that information can be included in a database along with similar information obtained from a population of mammals (e.g., healthy mammals and mammals with particular diseases or illnesses). Clustering algorithms can be used before or after normalization of the information within the database. Typically, normalization can allow for changes of each variable independent of the value of that variable. This analysis can be a hierarchical clustering analysis, a PCA analysis, or any analysis that groups individuals based on like expression values (or correlative values). Any future individual(s) so typed can be compared to the database individually or in groups. The clustering can produce individuals alike across all parameters and identify the group (or immune profile) that an individual belongs to.

As described herein, a mammal assigned to an immune profile can be expected to have an immune system respond similarly to other members with the same immune profile. For example, an individual with cancer belonging to a normal immune profile can be expected to respond to immune modulating therapies similar to a healthy person treated in the same manner.

As described herein, a human can have and/or can be classified as having a healthy immune system profile when whole blood from that human contains, per μL, from about 2500 to about 6500 granulocytes (e.g., from about 3000 to about 6000, from about 3500 to about 5500, or from about 4000 to about 5000 granulocytes), from about 1000 to about 2500 lymphocytes (e.g., from about 1250 to about 2250, from about 1500 to about 2000, or from about 1600 to about 1800 lymphocytes), from about 300 to about 700 monocytes (e.g., from about 350 to about 650, from about 400 to about 600, or from about 450 to about 550 monocytes), from about 800 to about 1700 T cells (e.g., from about 925 to about 1575, from about 1050 to about 1450, or from about 1100 to about 1400 T cells), from about 115 to about 400 B cells (e.g., from about 150 to about 350, from about 175 to about 325, or from about 200 to about 300 B cells), from about 100 to about 350 NK cells (e.g., from about 125 to about 325, from about 150 to about 300, or from about 175 to about 275 NK cells), from about 550 to about 1400 CD4$^+$ lymphocytes (e.g., from about 600 to about 1350, from about 650 to about 1300, or from about 700 to about 1250 CD4$^+$ lymphocytes), from about 10 to about 50 regulatory T cells (e.g., from about 15 to about 45, from about 20 to about 40, or from about 22 to about 34 regulatory T cells), from about 15 to about 90 CD14$^+$HLA-DR$^{lo/neg}$ monocytes (e.g., from about 25 to about 80, from about 35 to about 70, or from about 45 to about 57 CD14$^+$HLA-DR$^{lo/neg}$ monocytes), and from about 300 to about 600 CD86$^+$ monocytes (e.g., from about 340 to about 560, from about 380 to about 520, or from about 420 to about 480 CD86$^+$ monocytes). In some cases, a human can have and/or can be classified as having a healthy immune system profile when whole blood from that human contains the cell counts as set forth in Table 7 for healthy volunteers.

A mammal can have and/or can be classified as having an immune system profile 1 when whole blood from that mammal contains, per μL, from about 3000 to about 9000 granulocytes (e.g., from about 3750 to about 8250, from about 4500 to about 7500, or from about 5250 to about 6750 granulocytes), from about 950 to about 2500 lymphocytes (e.g., from about 1000 to about 2250, from about 1250 to about 2000, or from about 1400 to about 1800 lymphocytes), from about 350 to about 750 monocytes (e.g., from about 375 to about 700, from about 425 to about 600, or from about 500 to about 560 monocytes), from about 650 to about 1750 T cells (e.g., from about 800 to about 1600, from about 950 to about 1450, or from about 1100 to about 1300 T cells), from about 50 to about 400 B cells (e.g., from about 100 to about 350, from about 150 to about 300, or from about 200 to about 250 B cells), from about 100 to about 300 NK cells (e.g., from about 125 to about 275, from about 150 to about 250, or from about 175 to about 225 NK cells), from about 500 to about 1175 CD4$^+$ lymphocytes (e.g., from about 590 to about 1085, from about 680 to about 995, or from about 770 to about 905 CD4$^+$ lymphocytes), from about 5 to about 55 regulatory T cells (e.g., from about 10 to about 50, from about 15 to about 45, or from about 20 to about 40 regulatory T cells), from about 10 to about 185 CD14$^+$HLA-DR$^{lo/neg}$ monocytes (e.g., from about 30 to about 165, from about 50 to about 145, or from about 70 to about 125 CD14$^+$HLA-DR$^{lo/neg}$ monocytes), and from about 325 to about 650 CD86$^+$ monocytes (e.g., from about 365 to about 610, from about 405 to about 570, or from about 445 to about 530 CD86$^+$ monocytes). In some cases, a human can have and/or can be classified as having an immune system profile 1 when whole blood from that human contains the cell counts as set forth in Table 7 for profile 1.

A mammal can have and/or can be classified as having an immune system profile 2 when whole blood from that mammal contains, per μL, from about 550 to about 10500 granulocytes (e.g., from about 1800 to about 9250, from about 3050 to about 8000, or from about 4300 to about 6750 granulocytes), from about 1300 to about 2600 lymphocytes (e.g., from about 1450 to about 2450, from about 1600 to about 2300, or from about 1750 to about 2150 lymphocytes), from about 250 to about 500 monocytes (e.g., from about 280 to about 470, from about 310 to about 440, or from about 340 to about 410 monocytes), from about 870 to about 1920 T cells (e.g., from about 1000 to about 1790, from about 1130 to about 1660, or from about 1260 to about 1530 T cells), from about 90 to about 360 B cells (e.g., from about 125 to about 325, from about 160 to about 290, or from about 195 to about 255 B cells), from about 40 to about 615 NK cells (e.g., from about 110 to about 545, from about 180 to about 475, or from about 250 to about 405 NK cells), from about 600 to about 1200 CD4$^+$ lymphocytes (e.g., from about 670 to about 1130, from about 740 to about 1060, or from about 810 to about 990 CD4$^+$ lymphocytes), from about 15 to about 45 regulatory T cells (e.g., from about 19 to about 41, from about 23 to about 37, or from about 27 to about 32 regulatory T cells), from about 3 to about 17 CD14$^+$HLA-DR$^{lo/neg}$ monocytes (e.g., from about 5 to about 15, from about 7 to about 13, or from about 9 to about 11 CD14$^+$HLA-DR$^{lo/neg}$ monocytes), and from about 230 to about 440 CD86$^+$ monocytes (e.g., from about 255 to about 415, from about 280 to about 390, or from about 305 to about 365 CD86$^+$ monocytes). In some cases, a human can have and/or can be classified as having an immune system profile 2 when whole blood from that human contains the cell counts as set forth in Table 7 for profile 2.

A mammal can have and/or can be classified as having an immune system profile 3 when whole blood from that mammal contains, per μL, from about 5350 to about 20250 granulocytes (e.g., from about 7200 to about 18400, from about 9050 to about 16550, or from about 10900 to about 14700 granulocytes), from about 1500 to about 3000 lymphocytes (e.g., from about 1680 to about 2820, from about 1860 to about 2640, or from about 2040 to about 2460 lymphocytes), from about 710 to about 1460 monocytes (e.g., from about 800 to about 1370, from about 890 to about 1280, or from about 980 to about 1190 monocytes), from about 1040 to about 2320 T cells (e.g., from about 1200 to about 2160, from about 1360 to about 2000, or from about 1520 to about 1840 T cells), from about 130 to about 560 B cells (e.g., from about 180 to about 510, from about 230 to about 460, or from about 280 to about 410 B cells), from about 90 to about 340 NK cells (e.g., from about 120 to about 310, from about 150 to about 280, or from about 180 to about 250 NK cells), from about 740 to about 1660 CD4$^+$ lymphocytes (e.g., from about 850 to about 1550, from about 960 to about 1440, or from about 1070 to about 1330 CD4$^+$ lymphocytes), from about 20 to about 90 regulatory T cells (e.g., from about 28 to about 82, from about 36 to about 74, or from about 44 to about 66 regulatory T cells), from about 280 to about 910 CD14$^+$HLA-DR$^{lo/neg}$ monocytes (e.g., from about 360 to about 830, from about 440 to about 750, or from about 520 to about 670 CD14$^+$HLA-DR$^{lo/neg}$ monocytes), and from about 600 to about 1320 CD86$^+$ monocytes (e.g., from about 690 to about 1230, from about 780 to about 1140, or from about 870 to about 1050 CD86$^+$ monocytes). In some cases, a human can have and/or can be classified as having an immune system profile 3 when whole blood from that human contains the cell counts as set forth in Table 7 for profile 3.

A mammal can have and/or can be classified as having an immune system profile 4 when whole blood from that mammal contains, per µL, from about 5900 to about 18900 granulocytes (e.g., from about 7520 to about 17280, from about 1940 to about 15660, or from about 10760 to about 14040 granulocytes), from about 515 to about 1020 lymphocytes (e.g., from about 575 to about 960, from about 635 to about 900, or from about 695 to about 840 lymphocytes), from about 370 to about 1200 monocytes (e.g., from about 470 to about 1100, from about 570 to about 1000, or from about 670 to about 900 monocytes), from about 340 to about 790 T cells (e.g., from about 395 to about 735, from about 450 to about 680, or from about 505 to about 625 T cells), from about 30 to about 190 B cells (e.g., from about 50 to about 170, from about 70 to about 150, or from about 90 to about 130 B cells), from about 20 to about 170 NK cells (e.g., from about 40 to about 150, from about 60 to about 130, or from about 80 to about 110 NK cells), from about 190 to about 510 CD4$^+$ lymphocytes (e.g., from about 230 to about 470, from about 270 to about 430, or from about 310 to about 390 CD4$^+$ lymphocytes), from about 5 to about 18 regulatory T cells (e.g., from about 7 to about 16, from about 9 to about 14, or from about 11 to about 12 regulatory T cells), from about 100 to about 750 CD14+HLA-DR$^{lo/neg}$ monocytes (e.g., from about 180 to about 670, from about 260 to about 590, or from about 340 to about 510 CD14$^+$ HLA-DR$^{lo/neg}$ monocytes), and from about 200 to about 1020 CD86$^+$ monocytes (e.g., from about 300 to about 920, from about 400 to about 820, or from about 500 to about 720 CD86$^+$ monocytes). In some cases, a human can have and/or can be classified as having an immune system profile 4 when whole blood from that human contains the cell counts as set forth in Table 7 for profile 4.

A mammal can have and/or can be classified as having an immune system profile 5 when whole blood from that mammal contains, per µL, from about 3300 to about 10000 granulocytes (e.g., from about 4100 to about 9200, from about 4900 to about 8400, or from about 5700 to about 7600 granulocytes), from about 200 to about 1100 lymphocytes (e.g., from about 300 to about 1000, from about 400 to about 900, or from about 500 to about 800 lymphocytes), from about 100 to about 400 monocytes (e.g., from about 140 to about 360, from about 180 to about 320, or from about 220 to about 280 monocytes), from about 50 to about 850 T cells (e.g., from about 150 to about 750, from about 250 to about 650, or from about 350 to about 550 T cells), from about 0 to about 200 B cells (e.g., from about 20 to about 180, from about 40 to about 160, or from about 60 to about 140 B cells), from about 20 to about 200 NK cells (e.g., from about 40 to about 180, from about 60 to about 160, or from about 80 to about 140 NK cells), from about 0 to about 900 CD4$^+$ lymphocytes (e.g., from about 120 to about 780, from about 240 to about 660, or from about 360 to about 540 CD4$^+$ lymphocytes), from about 0 to about 45 regulatory T cells (e.g., from about 6 to about 39, from about 12 to about 33, or from about 18 to about 27 regulatory T cells), from about 10 to about 140 CD14$^+$HLA-DR$^{lo/neg}$ monocytes (e.g., from about 25 to about 125, from about 40 to about 110, or from about 55 to about 95 CD14$^+$HLA-DR$^{lo/neg}$ monocytes), and from about 40 to about 350 CD86$^+$ monocytes (e.g., from about 80 to about 310, from about 120 to about 270, or from about 160 to about 230 CD86$^+$ monocytes). In some cases, a human can have and/or can be classified as having an immune system profile 5 when whole blood from that human contains the cell counts as set forth in Table 7 for profile 5.

In some cases, a mammal (e.g., a human) can be determined to have and/or can be classified as having an immune system profile 1, 2, 3, 4, or 5 by determining the ratio of (a) the number of CD4$^+$ lymphocytes, CD8$^+$ lymphocytes, regulatory T cells, B cells, NK cells, granulocytes, lymphocytes, monocytes, T cells, CD14$^+$HLA-DR$^{lo/neg}$ monocytes, and/or CD86$^+$ monocytes present within a unit volume (e.g., µL) of whole blood (e.g., fresh, un-manipulated whole blood) from the mammal being assessed to (b) the number of CD4$^+$ lymphocytes, CD8$^+$ lymphocytes, regulatory T cells, B cells, NK cells, granulocytes, lymphocytes, monocytes, T cells, CD14$^+$HLA-DR$^{lo/neg}$ monocytes, and/or CD86$^+$ monocytes present within a unit volume (e.g., µL) of whole blood (e.g., fresh, un-manipulated whole blood) from a population of healthy controls. For example, a human can have and/or can be classified as having an immune system profile 1 or 2 when whole blood from that human contains the cell counts as a ratio to the cell counts of a healthy human as set forth in Table 8 for profile 1 or 2.

The number of CD4$^+$ lymphocytes, CD8$^+$ lymphocytes, regulatory T cells, B cells, NK cells, granulocytes, lymphocytes, monocytes, T cells, CD14$^+$HLA-DR$^{lo/neg}$ monocytes, and/or CD86$^+$ monocytes present within a unit volume (e.g., µL) of whole blood (e.g., fresh, un-manipulated whole blood) can be determined using flow cytometry. For example, anti-CD4, anti-CD8, anti-CD86, anti-CD14, and anti-HLA-DR antibodies as well as the antibodies and reagents listed in Table 3 can be used to perform flow cytometry in order to determine the number of CD4$^+$ lymphocytes, CD8$^+$ lymphocytes, regulatory T cells, B cells, NK cells, granulocytes, lymphocytes, monocytes, T cells, CD14$^+$HLA-DR$^{lo/neg}$ monocytes, and CD86$^+$ monocytes present within a unit volume (e.g., µL) of whole blood. In some cases, immunological techniques such as ELISA or cell staining techniques can be used to determine the number of CD4$^+$ lymphocytes, CD8$^+$ lymphocytes, regulatory T cells, B cells, NK cells, granulocytes, lymphocytes, monocytes, T cells, CD14$^+$HLA-DR$^{lo/neg}$ monocytes, and/or CD86$^+$ monocytes present within a unit volume (e.g., µL) of whole blood (e.g., fresh, un-manipulated whole blood). In some cases, techniques such as polymerase chain reaction or array technologies can be used to determine the number of CD4$^+$ lymphocytes, CD8$^+$ lymphocytes, regulatory T cells, B cells, NK cells, granulocytes, lymphocytes, monocytes, T cells, CD14$^+$HLA-DR$^{lo/neg}$ monocytes, and/or CD86$^+$ monocytes present within a unit volume (e.g., µL) of whole blood (e.g., fresh, un-manipulated whole blood).

Mammals (e.g., humans) having immune system profile 1 or 2 can be healthy or can be likely to have a favorable medical outcome for a particular medical condition (e.g., cancer, autoimmunity, sepsis or wound healing). For example, a human diagnosed with cancer and determined to have immune system profile 1 as described herein can be classified as being likely to have a favorable medical outcome for that medical condition.

In some cases, the methods and materials provided herein can be used to associate the effect of immune modulating drugs with their effect on a particular mammal having a pre-determined immune profile independent of the underlying disease pathology.

This document also provides methods for treating mammals. For example, a human having glioblastoma can be treated by (a) performing flow cytometry using a blood sample obtained from that human to identify the human as having an immune system profile 1 or 2, and (b) administering surgery, radiation, or temazolimide to the human. In another example, a human having renal cell carcinoma can be treated by (a) performing flow cytometry using a blood sample obtained from that human to identify the human as having an immune system profile 1 or 2, and (b) administering surgery, IL-2, or cryotherapy. In another example, a human having non-Hodgkin lymphoma can be treated by (a) performing flow cytometry using a blood sample obtained from that human to identify the human as having an immune system profile 1 or 2, and (b) administering CHOP, RCHOP, or radiotherapy to the human.

The invention will be further described in the following examples, which do not limit the scope of the invention described in the claims.

EXAMPLES

Example 1—Peripheral Blood Immune Phenotypes and Multiparameter Analysis Reveal Prognostic Immune Profiles Independent of Underlying Cancer Diagnosis Patients and Healthy Volunteers Samples were collected, and previous results from typing peripheral blood for some glioblastoma (GBM) patients (Gustafson et al., *Neuro. Oncol.*, 12:631 (2010)), non-Hodgkin lymphoma (NHL) patients (Lin et al., *Blood*, 117:872 (2011)), and healthy volunteers were used for reanalysis in this study. Briefly, GBM patient samples were collected prior to surgery with or without concurrent steroids. NHL patients were newly diagnosed or recently relapsed patients off all chemotherapy for at least eight weeks. Patients with metastatic renal cell carcinoma (RCC) were newly diagnosed or had recent relapsed disease with samples taken before cytoreductive nephrectomy. Ovarian cancer patients were newly diagnosed or relapsed with no chemotherapy for the prior eight weeks. Specific characteristics are listed in Tables 1 and 2. Acute lung injury patients who presented with at least one risk factor for acute lung injury/acute respiratory distress syndrome (Iscimen et al., *Crit. Care Med.*, 36:1518 (2008)) within 12 hours of admission and/or recognition of the diagnosis were selected. Inclusion criteria were used as described according to the American-European Consensus Conference (Bernard et al., *Am. J. Crit. Care Med.*, 20:225 (1994)) and consisted of acute onset of hypoxemia (where $PaO_2/FiO_2 \leq 300$ is acute lung injury; where $\leq 200$ is acute respiratory distress syndrome) and diffuse radiologic infiltrates in the absence of left atrial hypertension. Risk factors included pneumonia, sepsis, pancreatitis, shock, aspiration, high risk surgery, and high risk trauma (Bauer et al., *Intensive Care Med.*, 37:721 (2011)). The age of the healthy volunteers was not different from each group except for RCC (FIG. 1).

TABLE 1

Overall Survival Multivariate Cox Models in Cancer Patients.

| Phenotype (cells/µL) | P value |
| --- | --- |
| Lymphocytes | 0.2382 |
| Granulocytes | 0.0611 |
| Monocytes | 0.0563 |
| CD4 | 0.2206 |
| CD8 | 0.8504 |
| Regulatory T cells | 0.9381 |
| CD14+HLA-DRlo/neg monocytes | 0.0348 |
| CD86+ monocytes | 0.2405 |
| B cells | 0.9646 |
| NK cells | 0.9071 |

TABLE 2

Ovarian cancer patient characteristics.

| Age | Diagnosis |
| --- | --- |
| 78 | high stage, high grade cc/serous morphology |
| 43 | stage IC, grade 3 serous |
| 63 | high stage, high grade primary peritoneal |
| 57 | mucinous cystadenoma |
| 40 | mucinous borderline arising in muc. Adenoma |
| 57 | stage IIIC grade 3 serous |
| 68 | stage IIIC high grade serous peritoneal primary |
| 65 | stage IIIC high grade serous |
| 55 | stage IC grade 3 serous/clear cell mix |
| 49 | stage IC grade 2 serous fallopian tube |
| 53 | stage 3C endo/clear cell mix |
| 63 | stage IIIC serous primary peritoneal |
| 58 | stage IIIC high grade serous |
| 29 | stage 3A grade 3 clear cell |
| 66 | stage 4 high grade serous peritoneal primary |
| 51 | stage 3B high grade serous/endometrioid mix |
| 58 | stage 3C grade 3 serous |

Flow Cytometry of Whole Blood

Peripheral blood was used as the source for antibody staining as described elsewhere (Gustafson et al., *Neuro Oncol.* 12:631 (2010); and Appay et al., *J. Immunol. Methods.*, 309:192 (2006)). Immune markers identified included granulocytes, lymphocytes, monocytes (identified by forward and side scatter), $CD3^+$ T cells, $CD19^+$ B cells, $(CD56^+)$ NK cells, $CD4^+$ T cells, regulatory T cells $(CD4^+ CD25^+CD127^{lo})$, $CD86^+$ total monocytes, and $CD14^+HLA-DR^{lo/neg}$ immunosuppressive monocytes. Antibody reagents are listed in Table 3. Becton Dickinson TruCount™ tubes were used to collect cell counts/µL of blood for T, B, and NK cells. The remaining markers were measured as a percent of these cells by adding fluorochrome-conjugated antibodies that were directly added to 50-100 µL, of whole blood and incubated for 15-20 minutes at room temperature in the dark. RBCs were lysed with BD FacsLysis Solution (Becton Dickinson) per the manufacturer's instructions. Cells were centrifuged, washed with PBS, and fixed in 4% paraformaldehyde. Data were acquired on a Becton Dickinson FACSCalibur™ flow cytometer calibrated the day of use and analyzed with Cell Quest, Multiset (Becton Dickinson), and/or Flowjo (Ashland, Oreg.) software. Descriptions of gating strategies are listed in Table 4. The cell counts of granulocytes, lymphocytes, and monocytes were combined in each profile, and the average was plotted as pie graphs to represent the total population of circulating immune cells. The cell counts of $CD4^+$ cells, $CD8^+$ cells, B cells, NK cells, regulatory T cells, and $CD14^+HLA-DR^{lo/neg}$ monocytes, and $HLA-DR^{lo}$ monocytes were combined, and the average plotted as a pie graph to represent the total circulating mononuclear cells. CD8 cells were reported as the difference of CD3 and CD4 cells. CD14$^+$HLA-DR$^{lo/neg}$ and HLA-DR$^{lo}$ monocytes were calculated from the percentage of CD14$^+$ monocytes of total monocytes cell count (by forward/side scatter) and multiplied by the percentage of HLA-DR$^+$ and HLA-DR$^{lo}$ cells.

TABLE 3

Immune Phenotyping Reagents.

| Reagents/Antibodies | Company | Catalog number |
|---|---|---|
| FACS ™ Lysing Solution | BD | 349202 |
| Trucount ™ tubes | BD | 340334 |
| BD Multitest CD3/CD16$^+$/CD56/CD45/CD19 | BD | 340500 |
| CD127 PE | BD | 557938 |
| CD4 PerCP | BD | 340671 |
| CD25 APC | BD | 555434 |
| CD3 FITC | BD | 349201 |
| CD3 PE | BD | 340662 |
| CD3 PerCP | BD | 340663 |
| CD3 APC | BD | 340440 |
| CD4 FITC | BD | 555346 |
| CD8 PE | BD | 340046 |
| CD28 APC | BD | 559770 |
| CD152 (CTLA4) PE | BD | 555853 |
| CCR7 FITC | R&D Systems | FAB197F |
| CD62L APC | BD | 559772 |
| CD45RO | BD | 347967 |
| CD8 PerCp | BD | 347314 |
| IgG FITC | BD | 349041 |
| IgG PE | BD | 340761 |
| IgG PERCP | BD | 349044 |
| IgG APC | BD | 340754 |
| CD14 APC | BD | 555399 |
| HLA-DR PerCP | BD | 347364 |
| CD80 FITC | BD | 555683 |
| CD86 PE | BD | 555658 |
| Lineage FITC | BD | 340546 |
| CD33 APC | BD | 551378 |
| CD16 PE | eBioscience | 12-0168-73 |

TABLE 4

Gating instructions for selected immune phenotypes (26 tubes).

| Phenotype | Antibodies | Gating strategy |
|---|---|---|
| Granulocytes, Lymphocytes, Monocytes | | Gate total leukocytes<br>Gate G, L, M by forward and side scatter. |
| Regulatory T-cells | CD4, CD3, CD127, and CD25 | Gate lymphocytes<br>Plot CD4/forward scatter - Gate CD4$^+$<br>Plot CD 25 vs. CD127 |
| Co-Stimulatory and Inhibitory molecules on T-cells | CD28, CD4, CD8, and CTLA4 | Gate lymphocytes<br>Plot CD4/forward scatter - Gate CD4$^+$<br>Plot CD28 vs. CTLA4<br>Plot CD8/forward scatter - Gate CD8$^+$<br>Plot CD28 vs. CTLA4 |
| Central and Effector Memory CD4 Helper Cells | CD4, CD45RO, CD62L, and CCR7 | Gate lymphocytes<br>Plot CD4/CD45RO - Gate CD4$^+$/CD45RO$^+$<br>Plot CD62L vs. CCR7 |
| Central and Effector Memory CD8 Helper Cells | CD8, CD45RO, CD62L, and CCR7 | Gate lymphocytes<br>Plot CD8/CD45RO - Gate CD8$^+$/CD45RO$^+$<br>Plot CD62L vs. CCR7 |
| Classical, Intermediate, and Non-Classical Monocytes | CD14, CD16, and HLA-DR | Gate monocytes<br>Plot CD14/CD16–<br>Geometric mean (MFI) - HLA-DR<br>Plot HLA-DR vs. CD14 |
| CD14+/HLA DR low/neg. monocytes | CD14 and HLA-DR | Gate monocytes<br>Gate CD14$^+$ cells<br>Plot CD14 vs. HLA-DR |
| CD86+ monocytes | CD86 | Gate monocytes<br>Gate CD86$^+$ cells |
| Myeloid derived suppressor cells | Lineage, CD33, and HLA-DR | Gate peripheral blood mononuclear cells by forward and side scatter<br>Gate lineage neg cells<br>Plot CD33 vs. HLA-DR<br>Report CD33$^+$/DR$^{neg}$ as a percent of PBMC's |

Multiparameter Analysis and Hierarchical Clustering

Immune marker values were either measured directly in cells/µL or converted into cells/µL using the T, B, or NK counts. Mean values of each immune marker were determined using the values from 40 healthy volunteers. Each immune marker for each individual (healthy volunteers and patients) was then normalized by dividing the individual value by the mean value of healthy volunteers of that marker. The marker ratios for each volunteer and patient were imported into Partek Genomics Suite 6.5 software (Partek Inc., St. Louis, Mo.) and log-transformed for hierarchical clustering. Hierarchical analysis was performed by unsupervised agglomerative Euclidean average linkage clustering. Principal component analysis was performed using the Scatter plot view in the Partek program. Immune phenotypes as defined herein were the number and composition of circulating white blood cells within an individual. An immune profile was a group of immune phenotypes (containing a minimum of seven members) with as few dendrogram branches as possible. Additionally, all diseased members within a profile were compared to diseased members of other profiles (unless indicated) to determine profile differences.

Statistical Analyses

Values for subgroups of data were tested for statistical significance using the two-tailed non-parametric Mann-Whitney test for unpaired samples, the non-parametric Spearman correlation test for correlative analyses, and the Fisher's 2×2 or 3×3 exact test for distribution between profiles. Cox models were used to identify prognostic factors for overall survival, where the models were adjusted for age and stratified by disease. The method of Contal and O'Quigley was used to determine a best cut-point for the $CD4^+/CD14^+HLA-DR^{lo/neg}$ monocyte ratio (Contal and O'Quigley, Comput. Stat. Data Analysis, 30:253 (1999)). Overall survival was evaluated using standard Kaplan-Meier methods. All statistical analyses and graphs were performed using Prism, version 5.0 software (GraphPad Software, San Diego, Calif.) and SAS software (SAS Institute Inc., Cary, N.C.).

Identification of Distinct Immune Profiles within Diseases

The number and relative composition of ten immune markers in peripheral blood of healthy volunteers (HV) and patients were assessed. These markers provided a comprehensive overview of the immune system with unambiguous gating strategies or had clearly defined functions related to immune suppression (Gustafson et al., Neuro. Oncol., 12:631 (2010); and Banham, Trends Immunol., 27:541 (2006)). To reduce the dimensionality of information and to cluster potentially similar immune phenotypes, cell counts were measured or calculated, normalized to that of healthy volunteers, and analyzed using hierarchical clustering and principal component analysis.

Figure 2A:
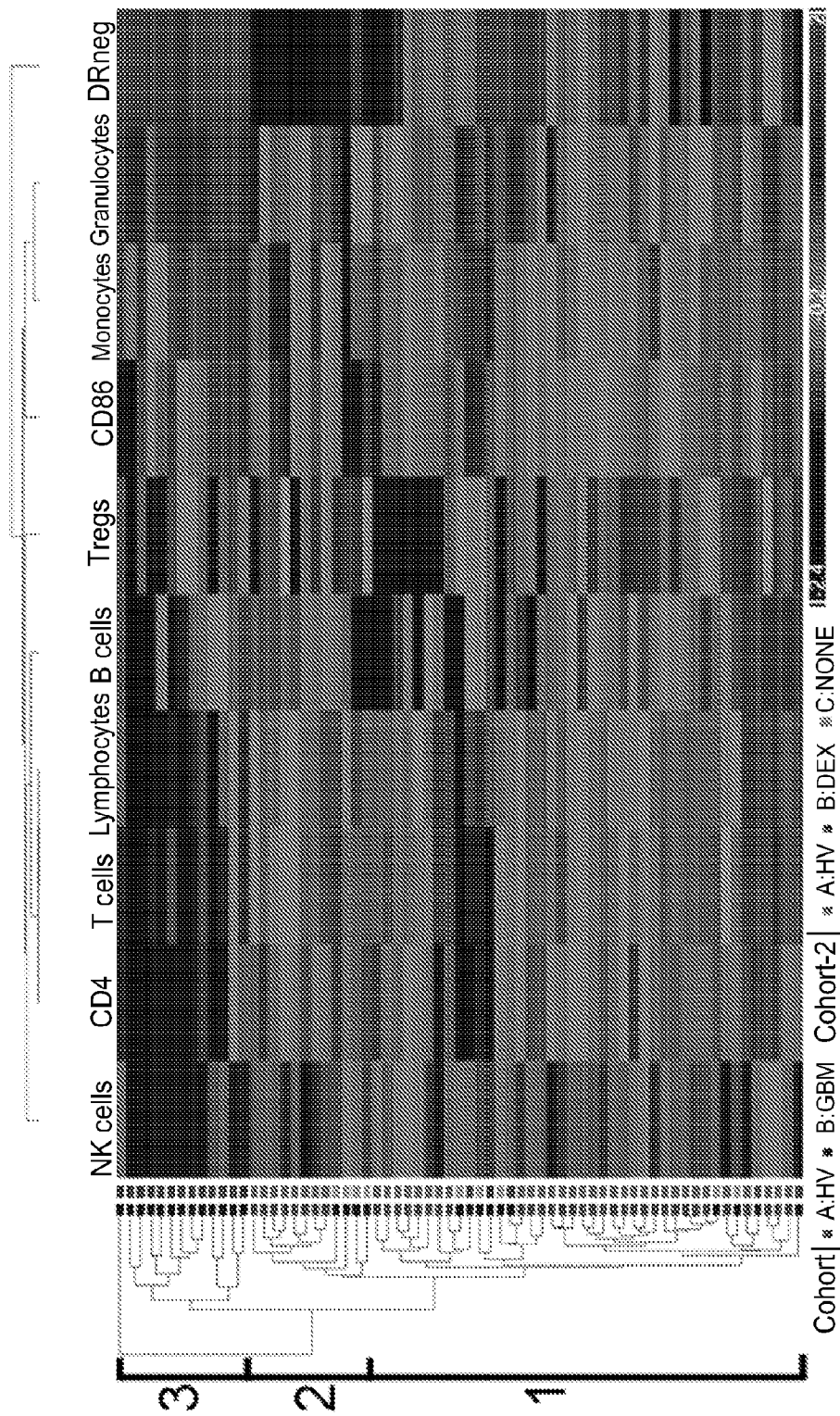
FIGS. 2A-2E are graphs of hierarchical clustering identifying immune profiles within patient groups. Peripheral blood leukocyte populations were measured by flow cytometry. The number of cells/µL for each marker was determined directly or converted from TruCount™ tubes. All phenotype values were normalized against the mean of similarly measured and converted healthy volunteers (n=40). Unsupervised clustering was performed using ten immune markers. The same HV cohort was used for all clustering analysis. Identification of major clusters is indicated at left. A row represents one subject, and a column represents one of ten markers measured.

Immune phenotypes were clustered within individual malignancies using HV as a control group for clustering. Unsupervised hierarchical clustering was performed on 27 glioblastoma (GBM) patients with 40 healthy volunteers (FIG. 2A). Three high level profiles were identified. Profile 1 contained 32 healthy volunteers, 5 dexamethasone-(DEX) treated patients, and 5 untreated GBM patients. Profile 2 contained 8 volunteers and 4 untreated patients. Profile 3 contained only 13 DEX-treated GBM patients (p=<0.0001; Fisher's 3×3 exact test). The segregation of these patients based on DEX treatment agreed with the conventionally analyzed immune markers of these patients where it was found that DEX treatment associated with decreased T cell numbers and loss of HLA-DR expression on $CD14^+$ monocytes (Gustafson et al., Neuro Oncol., 12:631 (2010)). Thus, this hierarchical clustering identified previously known informative subgroups.

Figure 2B:
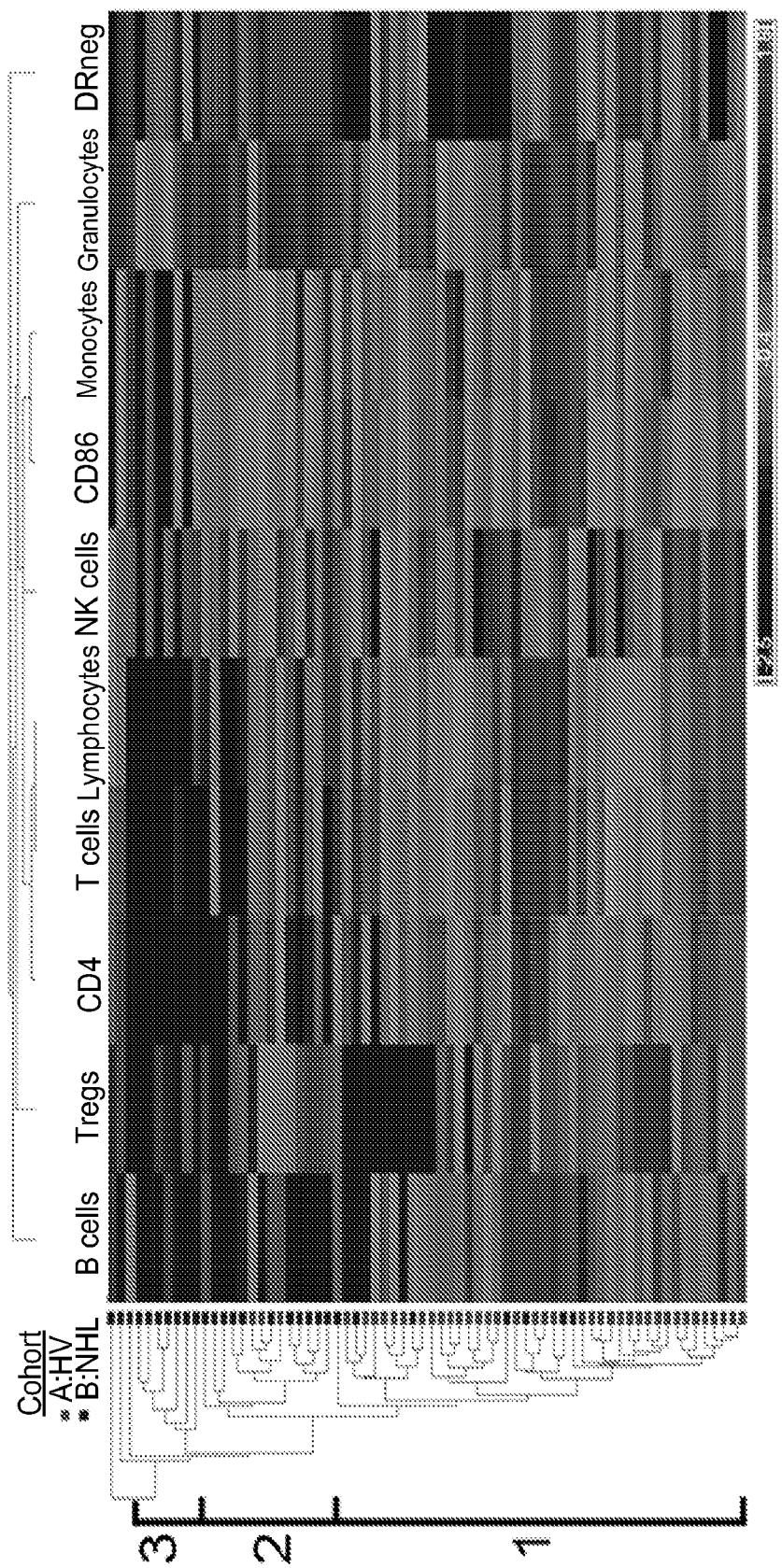
Figure 2C:
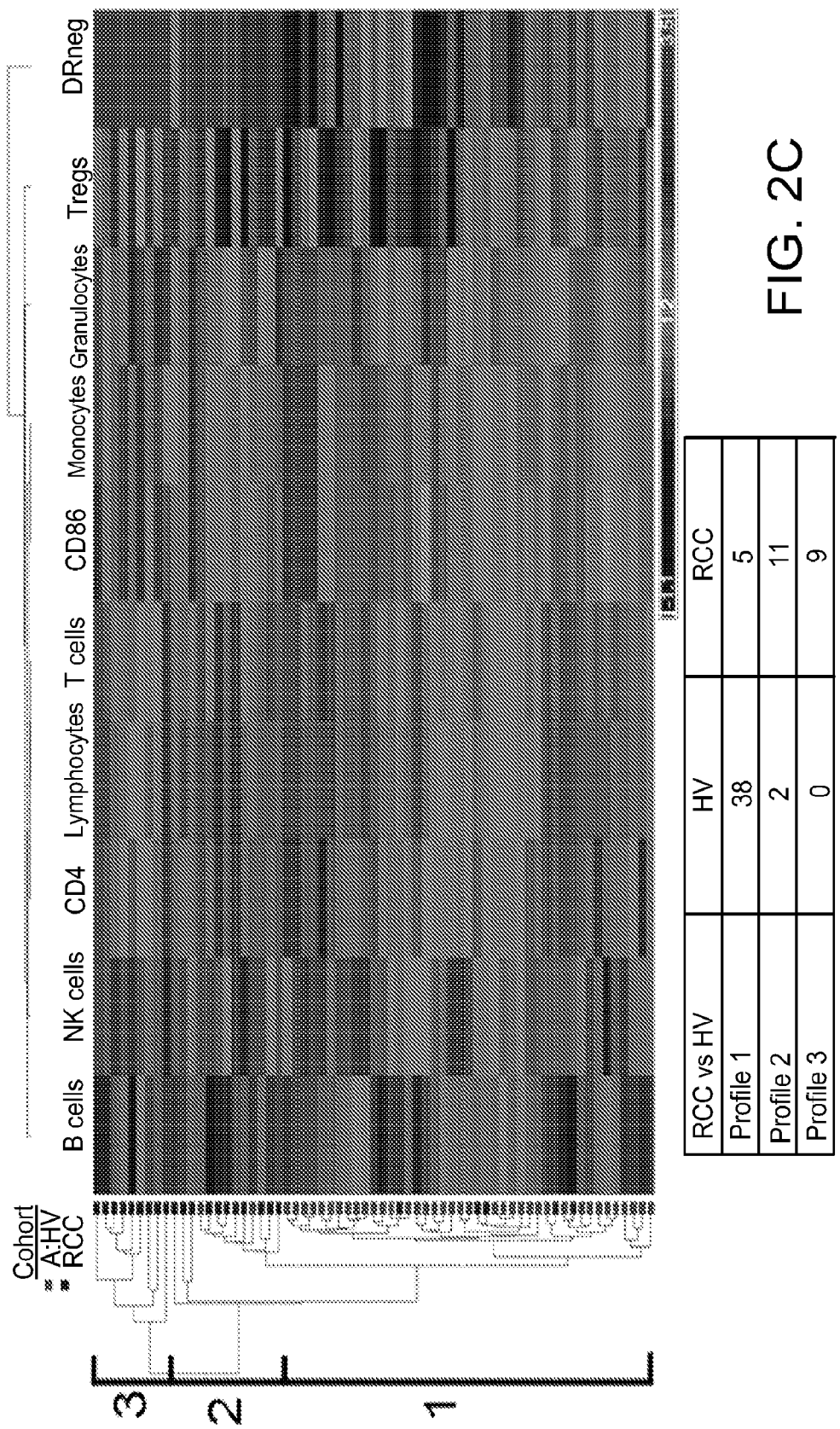
Figure 2D:
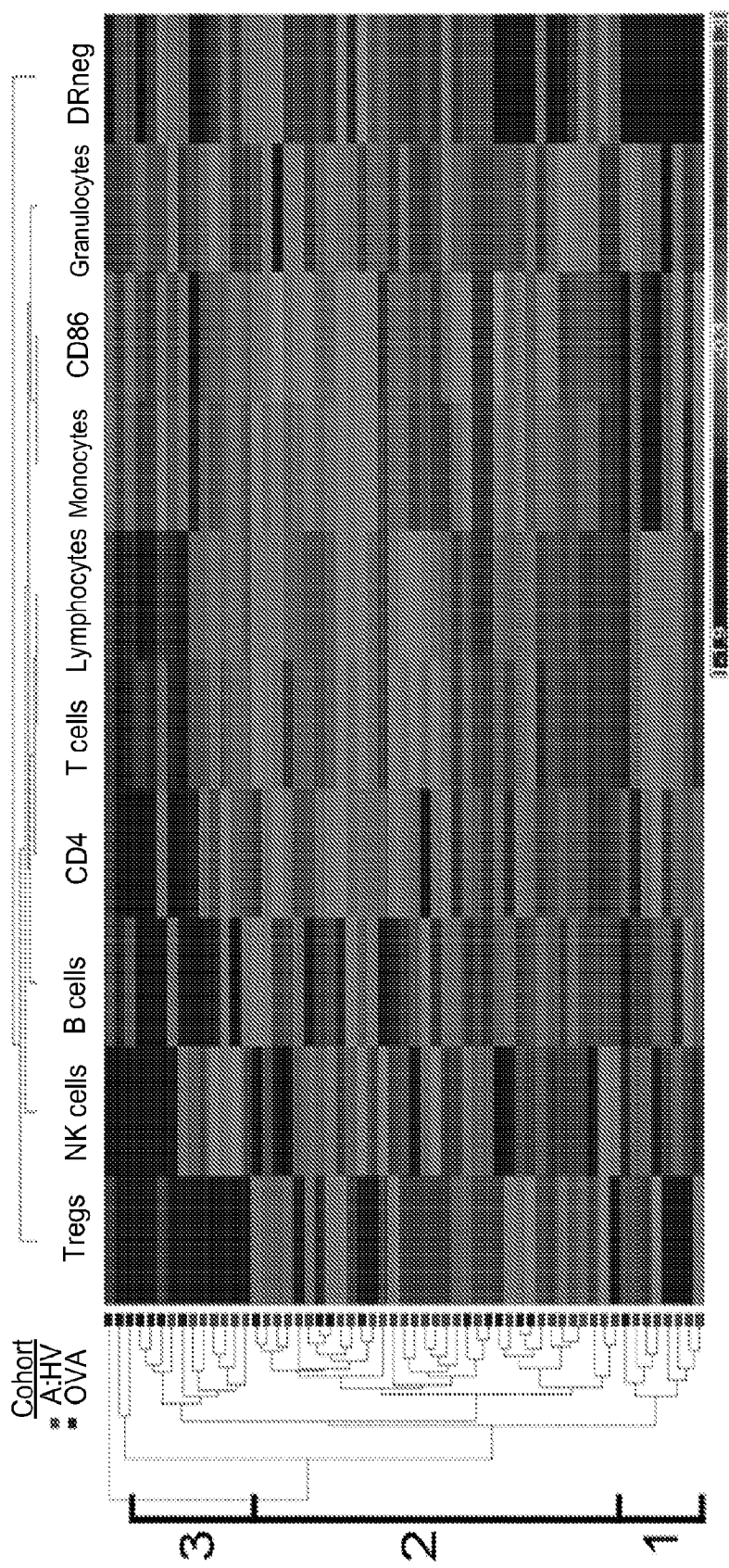

Patients with NHL, renal cell carcinoma (RCC), and ovarian cancer (OVA) were analyzed in a similar manner with the same set of healthy volunteers. Three profiles were assigned in NHL and RCC patients, and in each case, the majority of patients clustered in profiles separate from those with the HV profile (Profile 1) (FIGS. 2B and 2C). The OVA patients clustered across profiles with relatively equal distribution within the healthy volunteers, suggesting that this patient group most closely resembled a "normal" immune profile (FIG. 2D).

Figure 2E:
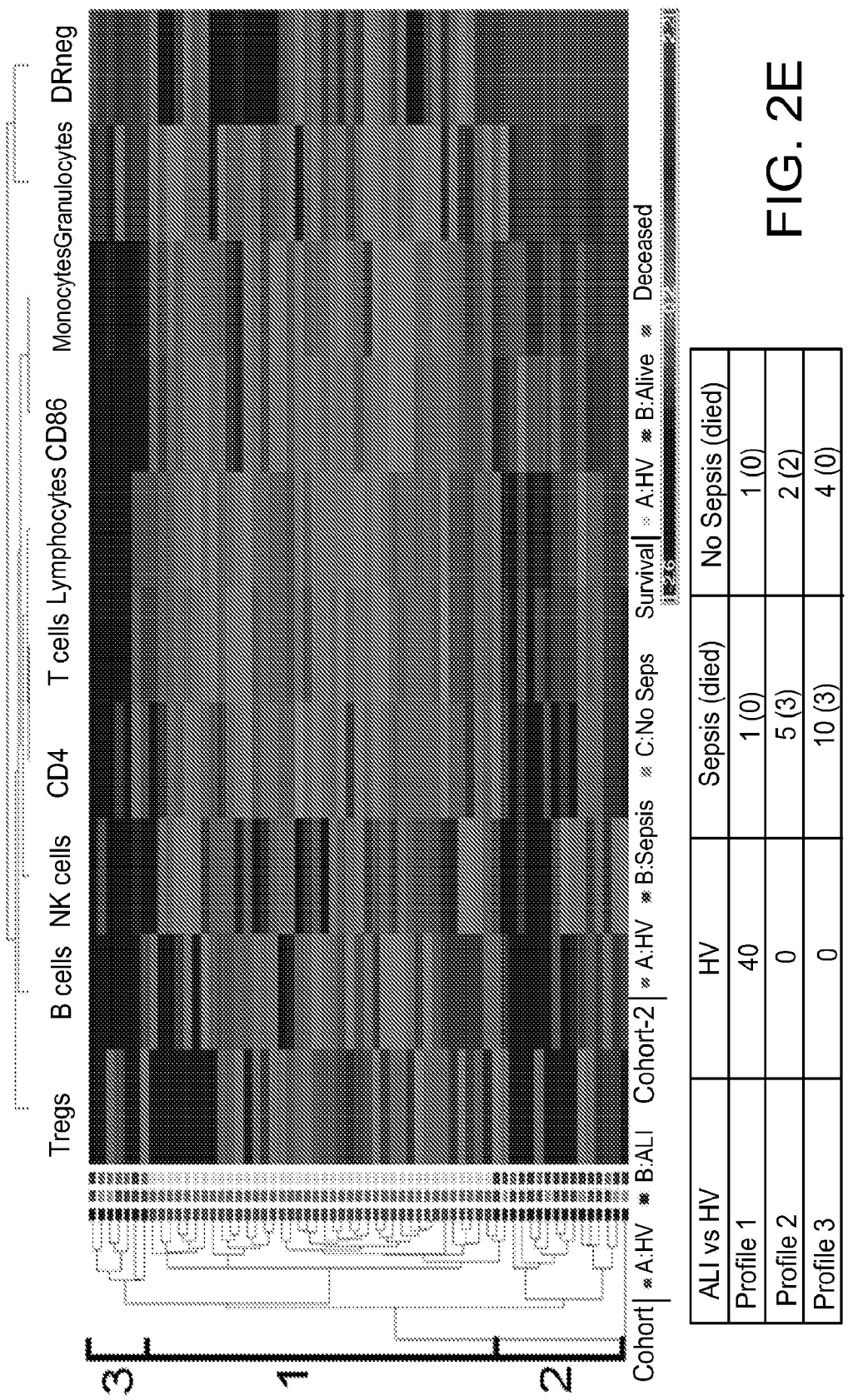

The immune phenotypes of acute lung injury patients (ALI) were analyzed. Many critically ill ALI patients had an initially strong pro-inflammatory response but quickly fell into a prolonged anti-inflammatory state called immune paralysis (Rittirsch et al., Nat. Rev. Immunol., 8:776 (2008); and Moore et al., J. Trauma, 40:501 (1996)). This patient population with or without concurrent sepsis was used as an additional valuable test of this approach in a non-malignant condition. There were three clearly identifiable profiles. Profile 1 contained all volunteers and no ALI patients. Profile 2 contained 7 ALI patients (5 septic). Profile 3 contained 16 ALI patients (11 septic) (FIG. 2E). Profiles 2 and 3 did not exhibit differences in the distribution of septic patients. However, patients in Profile 2 exhibited a lower survival rate than Profiles 1 and 3 in that 71% of patients in Profile 2 died from their condition, whereas only 19% of patients in Profiles 1 and 3 died (p=0.026). Taken together, these results indicate that hierarchical clustering can identify unique immune profiles for each disease group and that these profiles correlate with overall immune status (such as GBM patients receiving immune suppressive treatments) and clinical outcome (such as survival in ALI).

Identification of Distinct Immune Profiles Across Several Diseases

Assigned profiles within each cancer type and ALI differed regarding the underlying immune characteristics (e.g., Profile 2 in GBM did not share the same immune markers or quantities of cells as Profile 2 in NHL or RCC). The power of hierarchical clustering to segregate informatively immune phenotypes was dependent on the number of the individuals used in the analysis. To enhance the ability to identify immune profiles that represent a common immune status, these assays were repeated in an analysis that combined all healthy volunteers and patients.

Figure 3A:
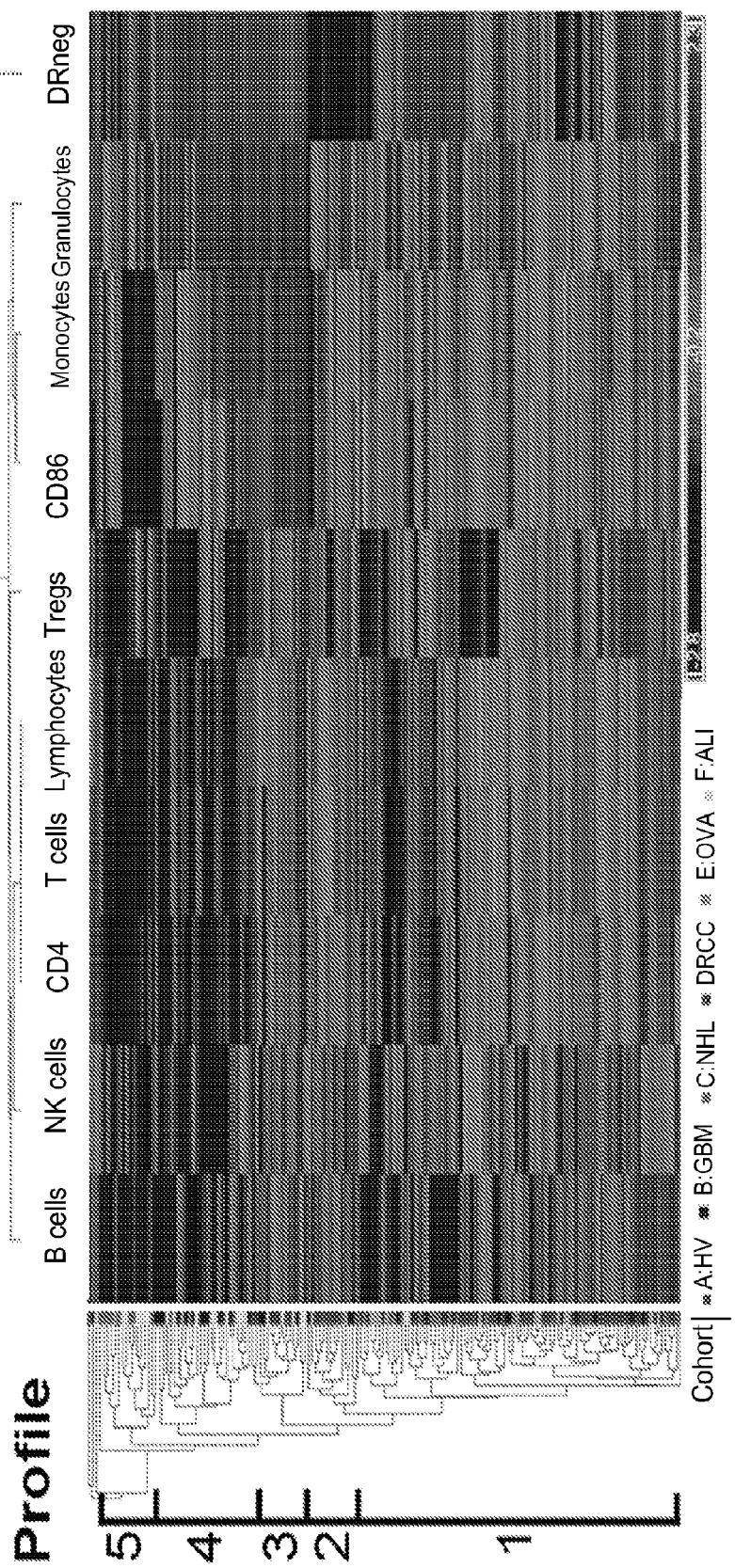

Five major profiles with at least 10 patients were identified (labeled 1-5) (FIG. 3A). Immune cell demographics are shown in FIG. 3B. All healthy volunteers were clustered within two immune profiles. The distribution of subjects among immune profiles was different for each malignancy or ALI yet some conditions had patients represented in each immune profile. These results suggest the existence of distinct profiles of immunity shared across diseases with disease specific variation in profile distribution.

Figure 4A:
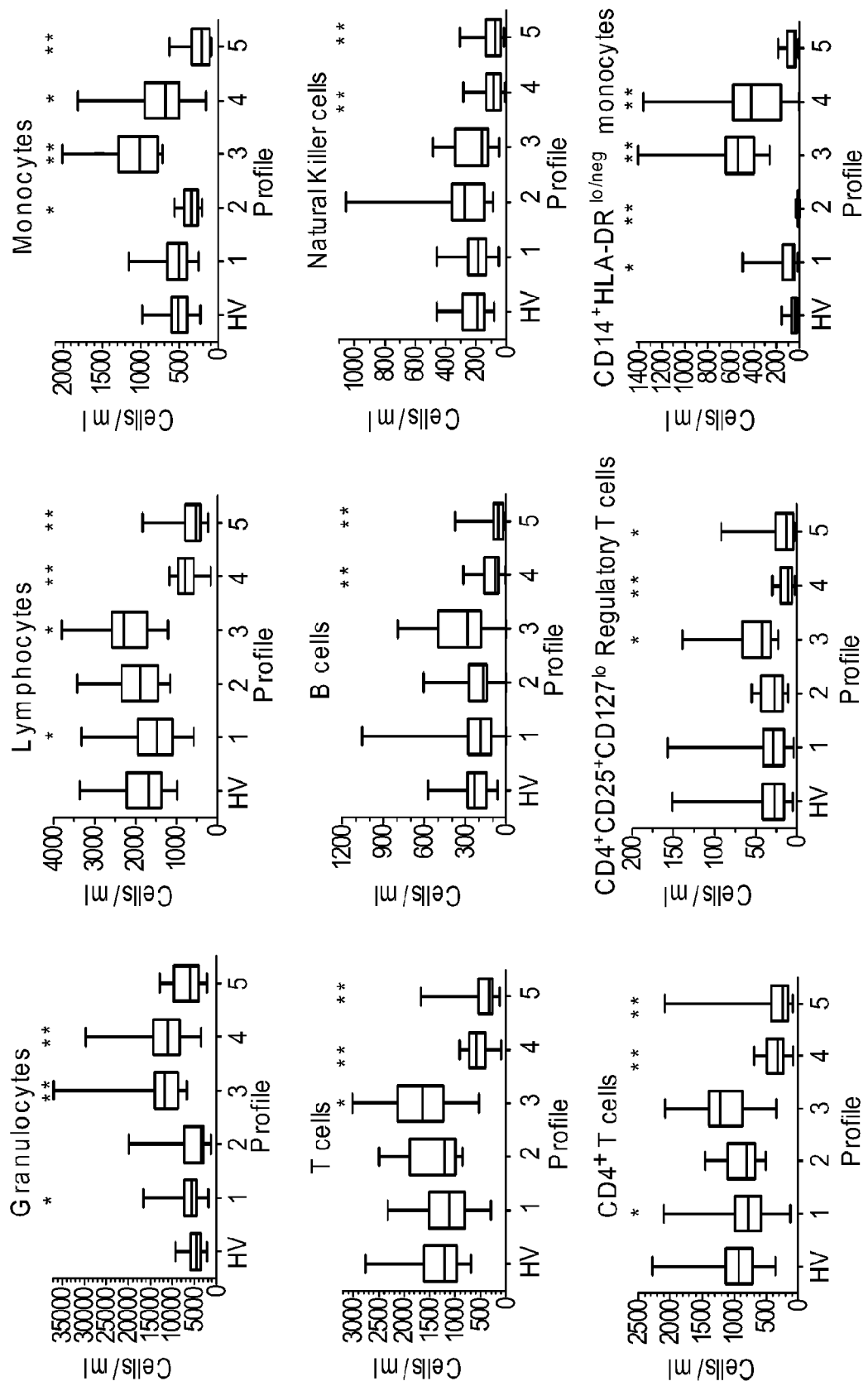

To confirm the uniqueness of each immune profile, the cell count data from each immune phenotype within each immune profile were used, and the values of each marker were compared to the values of the markers from other profiles or to only the pooled healthy volunteers (FIG. 4A and Table 5). The values of the markers from patients within Profiles 1 and 2 (where healthy volunteers typically segregate) were most similar to the healthy volunteers' pooled group. When compared to the pooled healthy volunteers, Profile 1 had fewer lymphocytes and elevated $CD14^+HLA-DR^{lo/neg}$ monocytes. Profile 2 had fewer monocytes and fewer $CD14^+HLA-DR^{lo/neg}$ monocytes when compared to the pooled healthy volunteers' profile. Profile 3 had elevated granulocytes, monocytes, and lymphocytes (mainly the T cell compartment) and elevated regulatory T cells and CD14$^+$HLA-DR$^{lo/neg}$ monocytes. Profile 4 had elevated granulocytes and monocytes, but decreased lymphocytes (including T, B, and NK cells), decreased CD4$^+$ T cells, and elevated CD14$^+$HLA-DR$^{lo/neg}$ monocytes. Abnormally low monocytes and lymphocytes including CD4$^+$ T cells were present in patients in Profile 5.

TABLE 5

P values for differences of immunophenotypes compared across profiles for FIG. 4A.

| | 1 | 2 | 3 | 4 | 5 |
|---|---|---|---|---|---|
| Granulocytes | | | | | |
| HV | 0.0093 | ns | <0.0001 | <0.0001 | ns |
| 1 | | 0.0414 | <0.0001 | <0.0001 | ns |
| 2 | | | 0.0009 | 0.0002 | ns |
| 3 | | | | ns | 0.0013 |
| 4 | | | | | 0.0015 |
| Lymphocytes | | | | | |
| HV | 0.0406 | ns | 0.0319 | <0.0001 | <0.0001 |
| 1 | | 0.404 | 0.0011 | <0.0001 | <0.0001 |
| 2 | | | ns | <0.0001 | <0.0001 |
| 3 | | | | <0.0001 | <0.0001 |
| 4 | | | | | 0.0371 |
| Monocytes | | | | | |
| HV | ns | 0.0021 | <0.0001 | 0.0018 | <0.0001 |
| 1 | | 0.0006 | <0.0001 | 0.0010 | <0.0001 |
| 2 | | | <0.0001 | 0.0001 | 0.0117 |
| 3 | | | | 0.0071 | <0.0001 |
| 4 | | | | | <0.0001 |
| T cells | | | | | |
| HV | ns | ns | 0.0270 | <0.0001 | <0.0001 |
| 1 | | ns | 0.0018 | <0.0001 | <0.0001 |
| 2 | | | ns | <0.0001 | <0.0001 |
| 3 | | | | <0.0001 | <0.0001 |
| 4 | | | | | 0.0359 |
| B cells | | | | | |
| HV | ns | ns | ns | <0.0001 | <0.0001 |
| 1 | | ns | 0.0393 | <0.0001 | <0.0001 |
| 2 | | | ns | 0.0057 | 0.0005 |
| 3 | | | | 0.0003 | 0.0003 |
| 4 | | | | | ns |
| NK cells | | | | | |
| HV | ns | ns | ns | <0.0001 | 0.0002 |
| 1 | | ns | ns | <0.0001 | 0.0002 |
| 2 | | | ns | 0.0002 | 0.0011 |
| 3 | | | | 0.0012 | 0.0072 |
| 4 | | | | | ns |
| CD4$^+$ T cells | | | | | |
| HV | 0.0274 | ns | ns | <0.0001 | 0.0002 |
| 1 | | ns | 0.0016 | <0.0001 | 0.0002 |
| 2 | | | ns | <0.0001 | 0.0001 |
| 3 | | | | <0.0001 | <0.0001 |
| 4 | | | | | ns |
| Regulatory T cells | | | | | |
| HV | ns | ns | .0050 | <0.0001 | 0.0146 |
| 1 | | ns | 0.0016 | <0.0001 | 0.0074 |
| 2 | | | ns | <0.0001 | 0.0001 |
| 3 | | | | <0.0001 | <0.0001 |
| 4 | | | | | ns |
| CD14$^+$HLA-DR$^{lo/neg}$ monocytes | | | | | |
| HV | 0.0022 | <0.0001 | <0.0001 | <0.0001 | ns |
| 1 | | <0.0001 | <0.0001 | <0.0001 | ns |
| 2 | | | <0.0001 | <0.0001 | 0.0001 |
| 3 | | | | ns | <0.0001 |
| 4 | | | | | <0.0001 |
| CD86$^+$ monocytes | | | | | |
| HV | ns | 0.0060 | <0.0001 | ns | <0.0001 |
| 1 | | 0.0010 | <0.0001 | ns | <0.0001 |
| 2 | | | <0.0001 | 0.0080 | 0.0061 |
| 3 | | | | 0.0019 | <0.0001 |
| 4 | | | | | <0.0001 | ns = p > 0.05

Figure 4B:
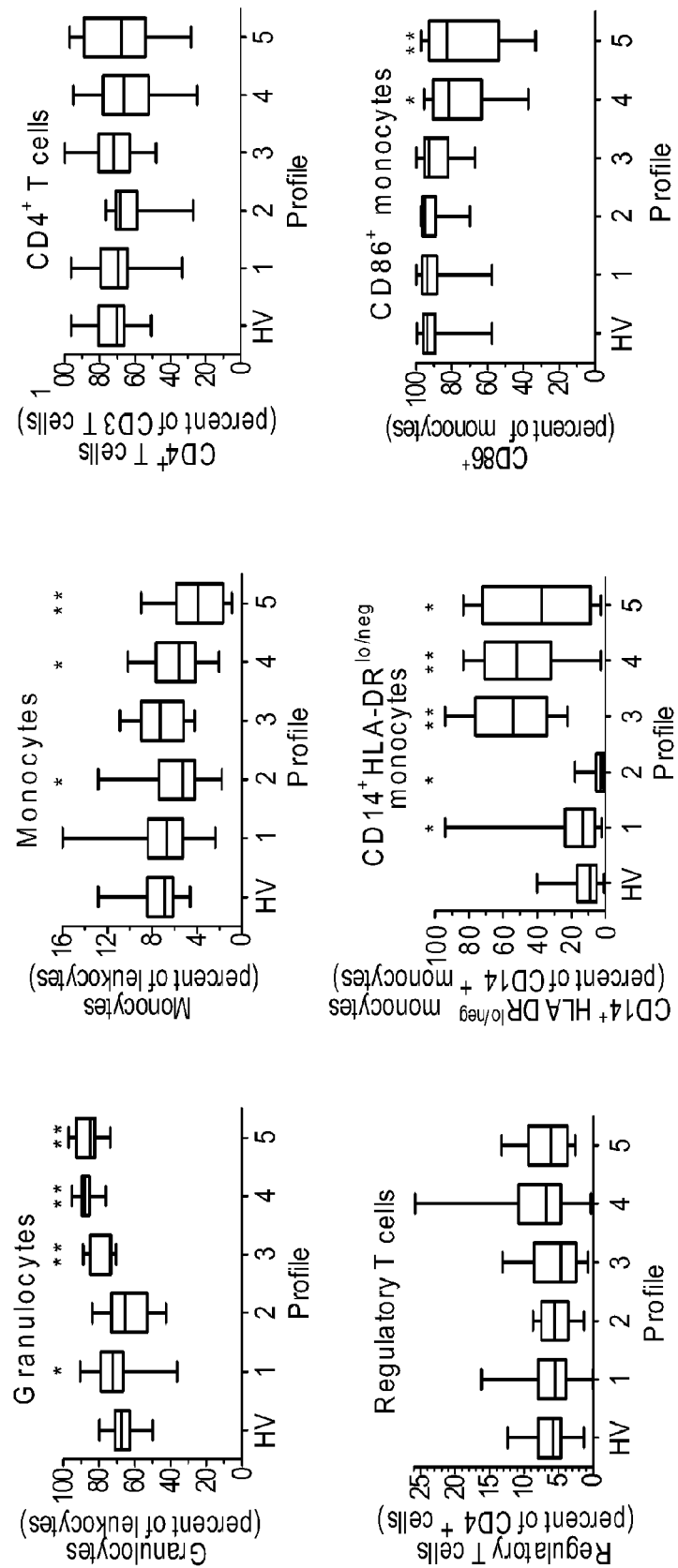

To evaluate the differences of immune profiles in relative quantities, the values from each immune phenotype were obtained, and the data were compared with values from the other profiles or the pooled healthy volunteers (FIG. 4B). This analysis confirmed that the profiles grouped subjects with similar immune profiles. Importantly, this method of analysis demonstrated that the profiles were identifying subjects with similar immune statuses representing both absolute and relative differences in key immune cells.

Figure 5:
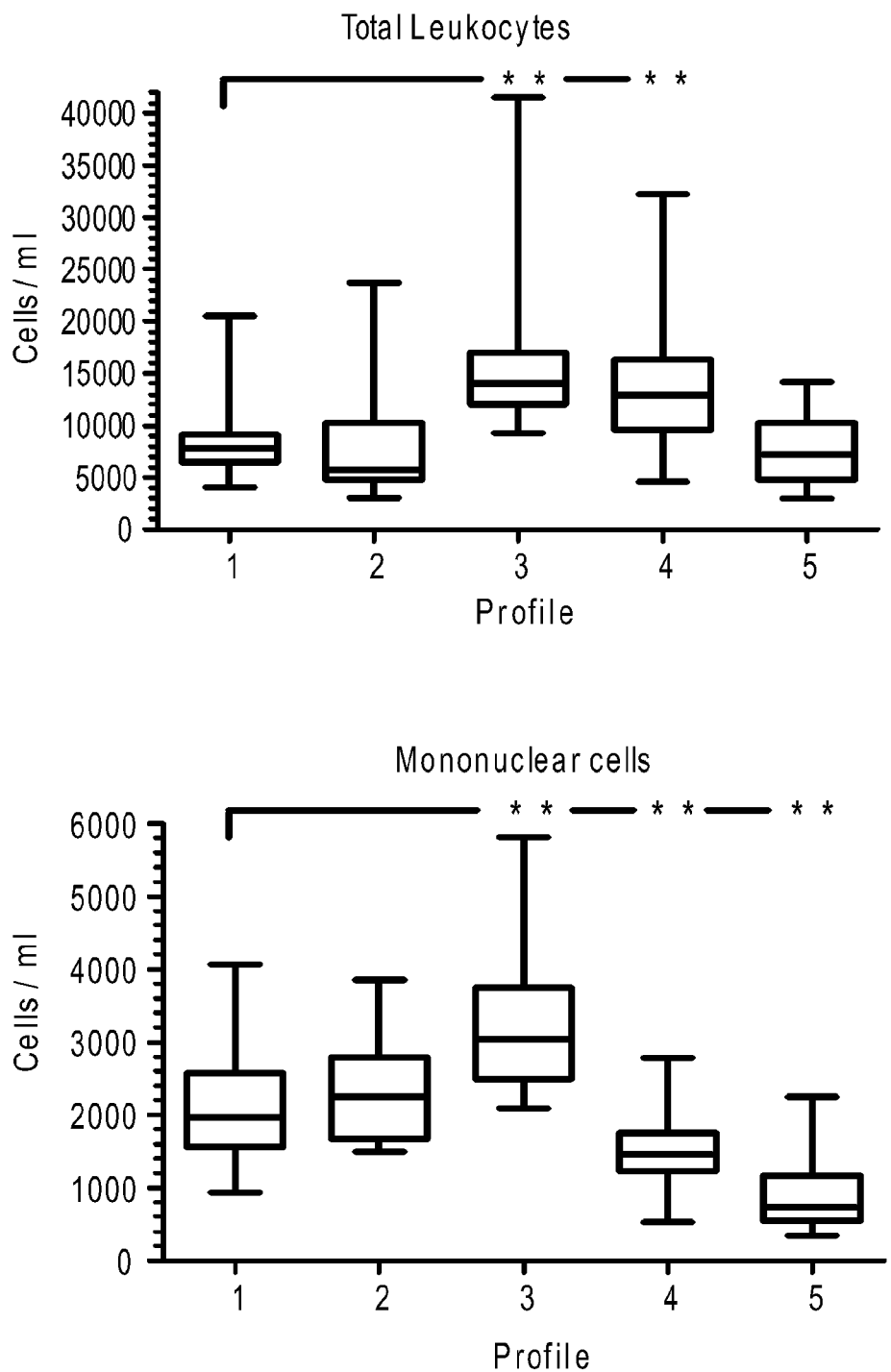
FIG. 5 contains graphs comparing total leukocyte and mononuclear cell counts (cells/µL) across profiles.

The data allowed the reconstruction of the average immune phenotype that exists within a profile. The average values of each of the immune markers (cells/μL) within an immune profile were used to reconstruct the composition of the average immune phenotype within that profile and plotted as a pie chart (FIG. 4C) for the entire leukocyte compartment and peripheral blood mononuclear cells (PBMC). The size of the pie chart reflected the relative quantity of cells per fixed unit of blood relative to Profile 1. For example, Profile 3 had almost twice as many total leukocytes as Profile 1 (p<0.0001 and FIG. 5), and Profile 4 had over 1.5 times that of Profile 1 (p<0.0001 and FIG. 5). This analysis allowed visualization of both relative and absolute values. The direction of the absolute change in total cells/μL was similar in all profiles except profile 4 where the leukocyte population increased while the PBMC population decreased. The magnitude of the difference also differed in the PBMC pools with Profile 3 having 1.5 times the amount of PBMCs than Profile 1 (p<0.0001 and FIG. 5) while Profile 5 had less than half of PBMCs than Profile 1 (p<0.0001 and FIG. 5). These results suggested that there exists peripheral blood immune profiles shared across disease states and that these profiles consisted of changes in the absolute and relative quantities of individual white blood cells.

Immune Profiles Correlate with Patient Outcome

Figure 6:
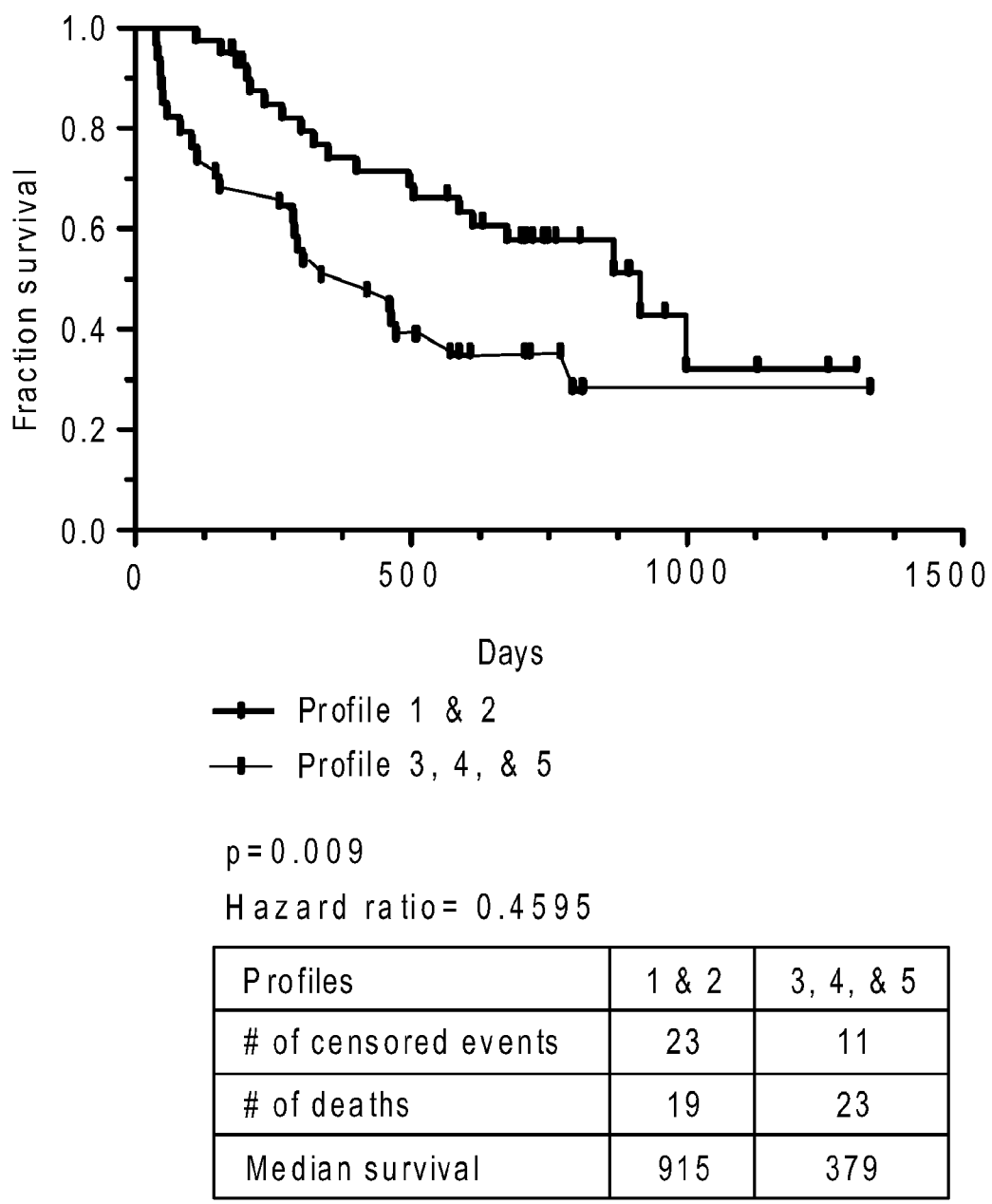
FIG. 6 contains survival data for GBM, NHL, and RCC patients based on immune profiles. Individual patients with GBM, NHL, or RCC with survival data were assigned a profile from FIG. 3. The survival data was adjusted to remove contributions of age and disease. Profiles 1 and 2 were grouped as they represent the only profiles seen in healthy volunteers and were compared to the survival of patients with profiles of 3, 4, and 5. Survival data were plotted for each immune profile regardless of underlying disease. P values were calculated by the Mantel-Cox log rank test.
Figure 7A:
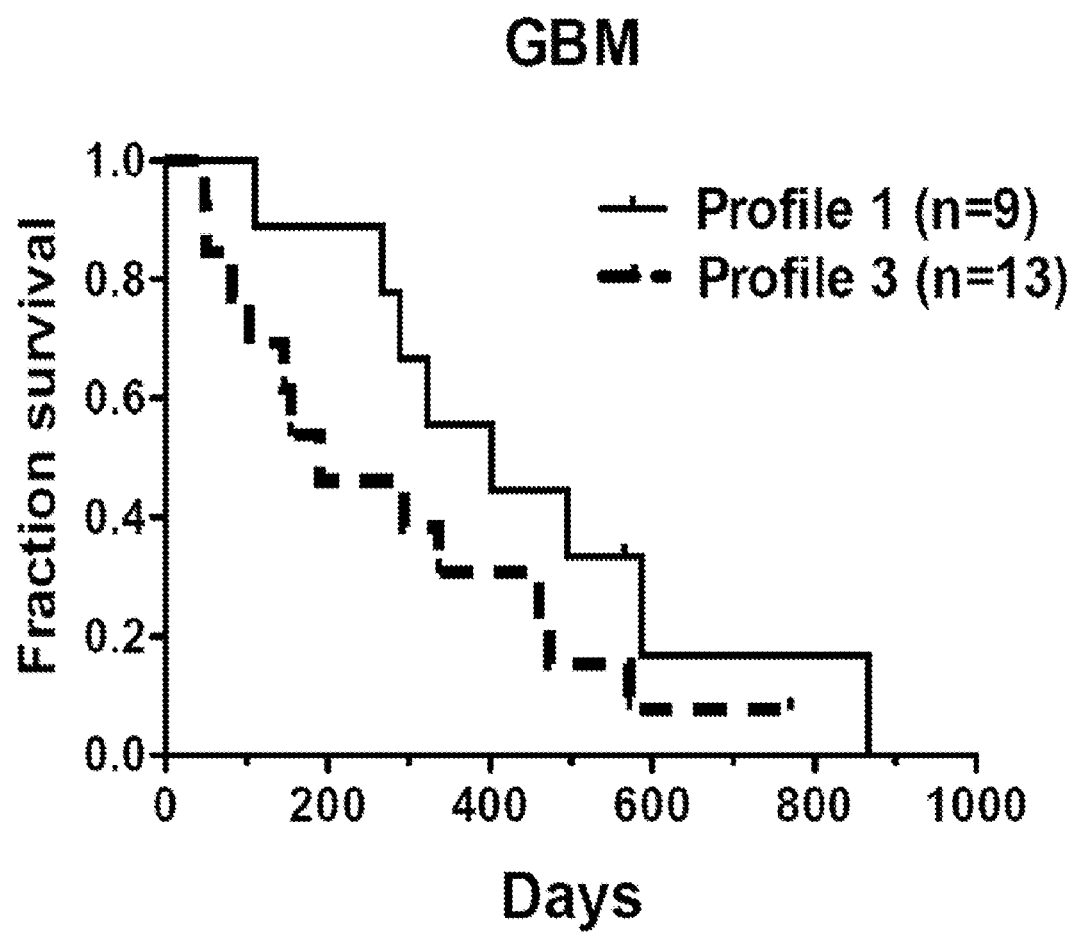
FIGS. 7A-D are graphs plotting the survival of patients categorized by immune profile in each indicated disease group.
Figure 7B:
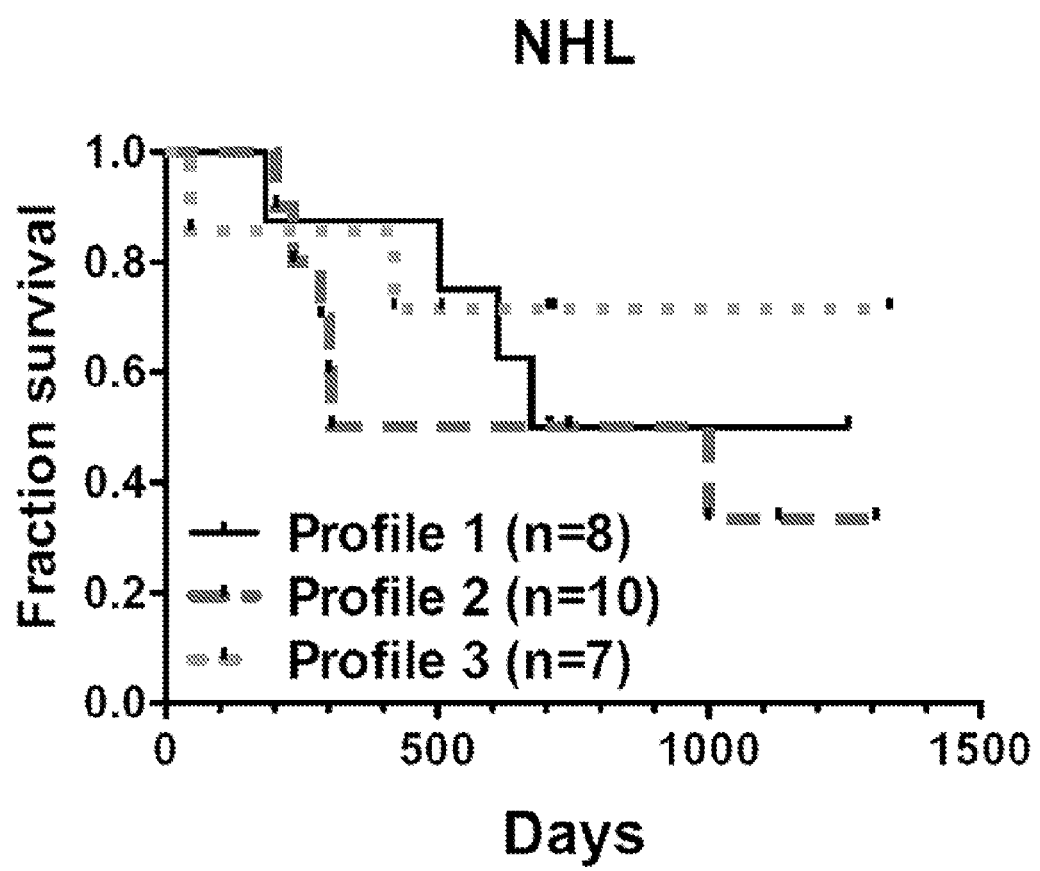
Figure 7C:
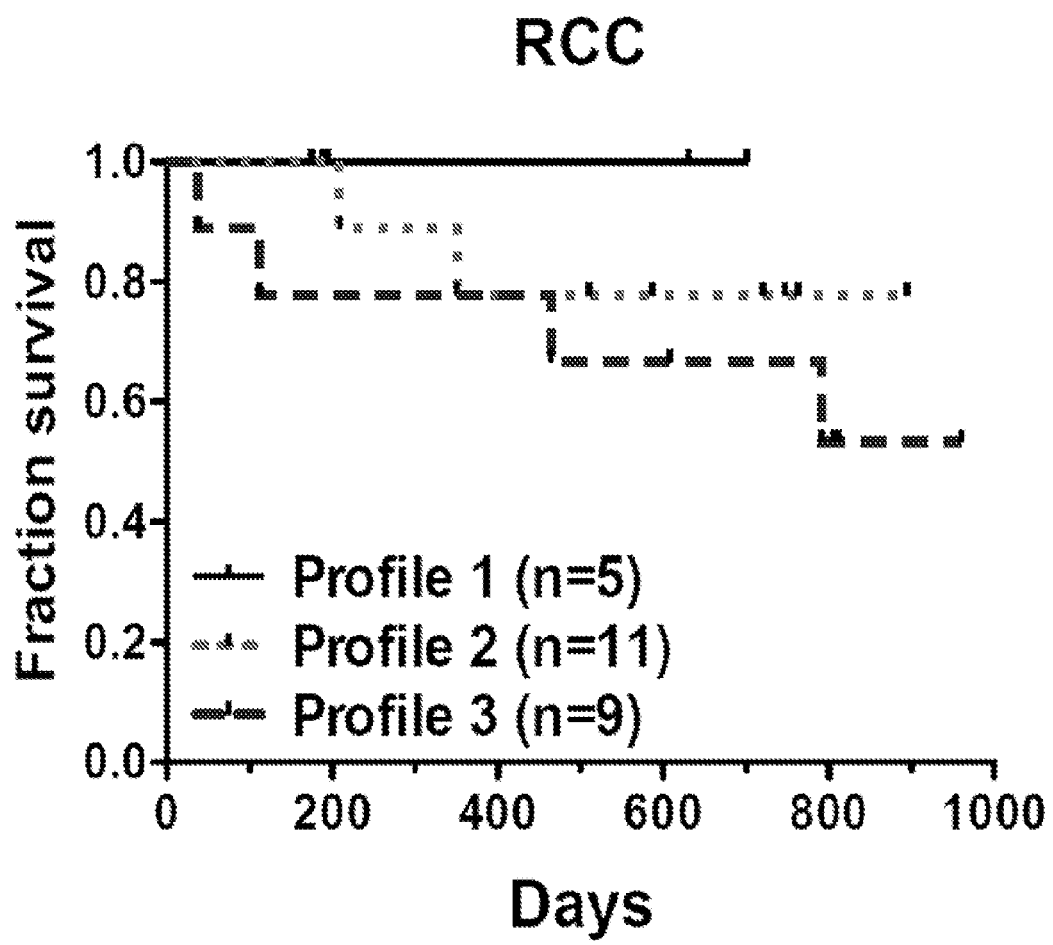
Figure 7D:
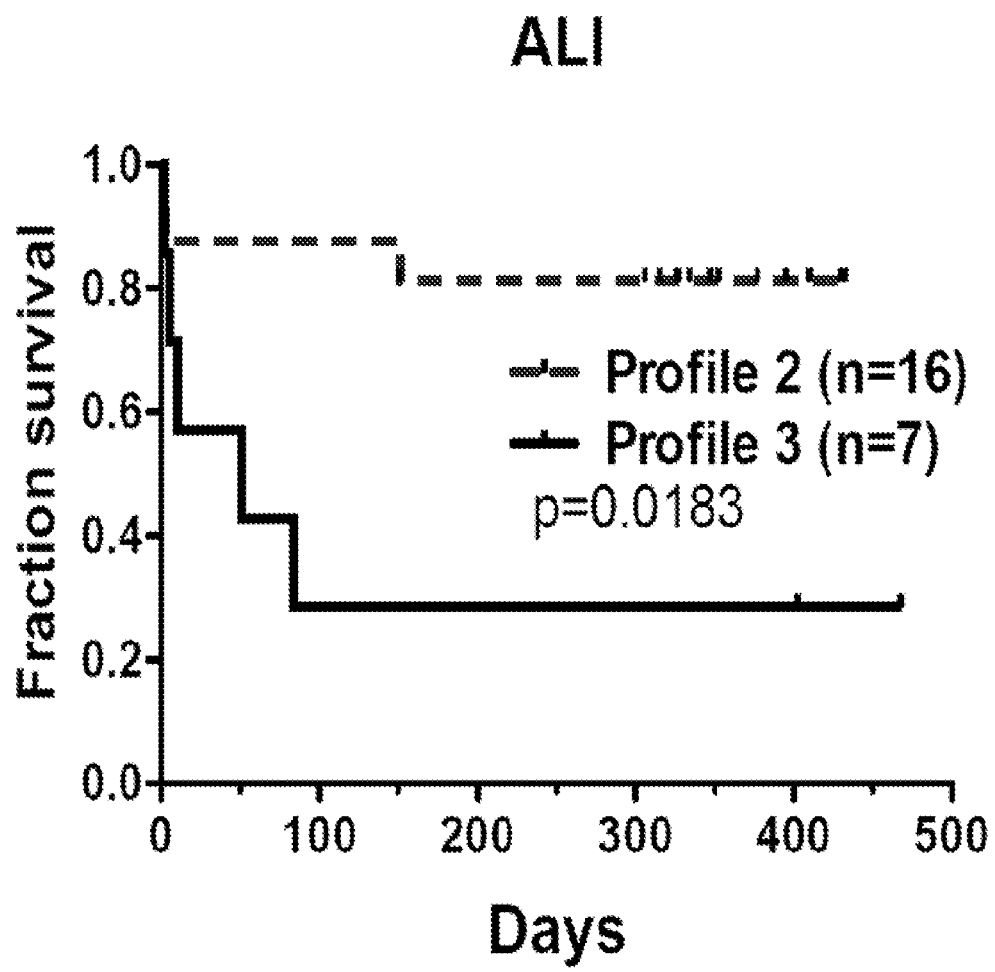

Immune profiles were predictive of survival in ALI (FIG. 2E). To see if immune profile predicted survival across cancer diagnosis, the data sets were used with survival data (GBM, NHL, and RCC patients). Patients were categorized by immune profile groups rather than cancer type, adjusting for age and cancer type. To provide sufficient samples, profiles were grouped as to those most closely resembling normal immune system and those that do not. As healthy volunteers were only grouped into Profiles 1 and 2, the patients found in these two immune profiles were pooled, and the overall survival of these patients was compared to those patients in the three remaining profiles (FIG. 6). The median overall survival of patients in Profile 1 and 2 (915 days, n=42) was almost two and a half times as long as those in the other immune profiles (379 days; n=34, p=0.009). In contrast, immune profiles identified within disease groups did not associate with survival (FIGS. 7A-D). It is clear that the unbiased approach presented herein segregated patients based solely on an unbiased immune status to identify those with the worst prognosis independent of underlying disease.
Identification of Related Immune Markers Using Hierarchical Clustering In addition to clustering individuals into immune profiles, hierarchical clustering identified immune markers related by their common presence across immune profiles. The common segregation of two immune markers was considered an immunological node. A subset of patients had been typed with a total of 23 immune markers. The previous analysis was repeated using these expanded immune markers to look at their potentially related distribution. Some relationships observed were expected including those where a marker was a large component of another marker such as T cells and lymphocytes, $CD4^+$ T cells with $CD28^+CD4^+$ T cells and central memory $CD4^+$ T cells (CD4Tcm), and $CD14^+CD16^-$ classical monocytes with $CD86^+$ monocytes (FIG. 5A). Some relationships were new such as granulocytes with $CD14^+HLA-DR^{lo/neg}$. Likewise, some considered related were not found together such as Tregs independent of other $CD4^+$ cells, and $CTLA4^+$ T cells independent of T cells. Lineage-HLA-DR-$CD33^+$ myeloid derived suppressor cells (MDSCs) clustered independently of both granulocytes and monocytes, suggesting independent regulation. Thus, this analysis produced correlative evidence of similar or disparate regulation of certain white blood cells in humans.

Figure 8A:
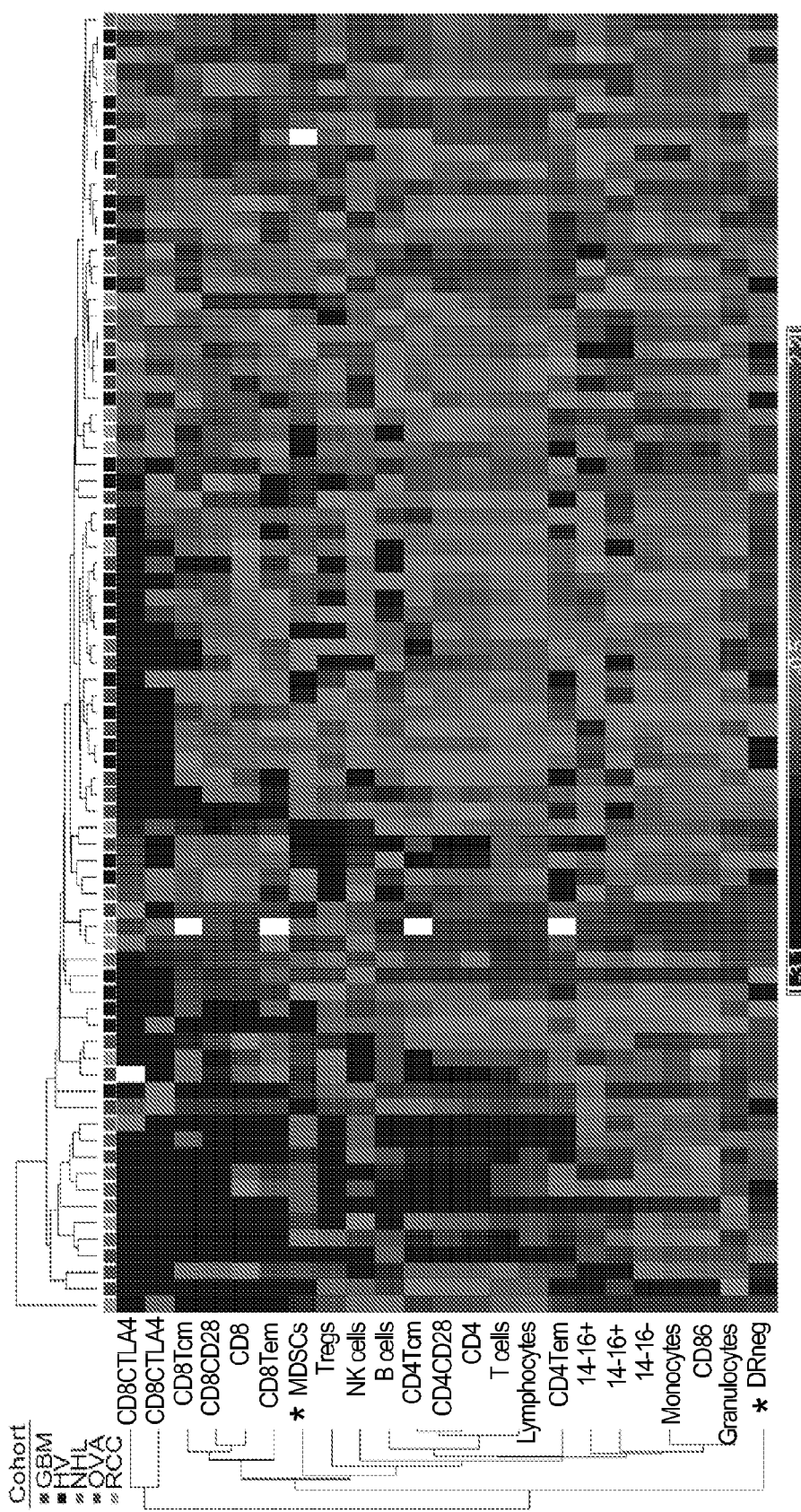
FIGS. 8A-8C contain data of hierarchical clustering identifying relationships between immune markers.
Figure 8B:
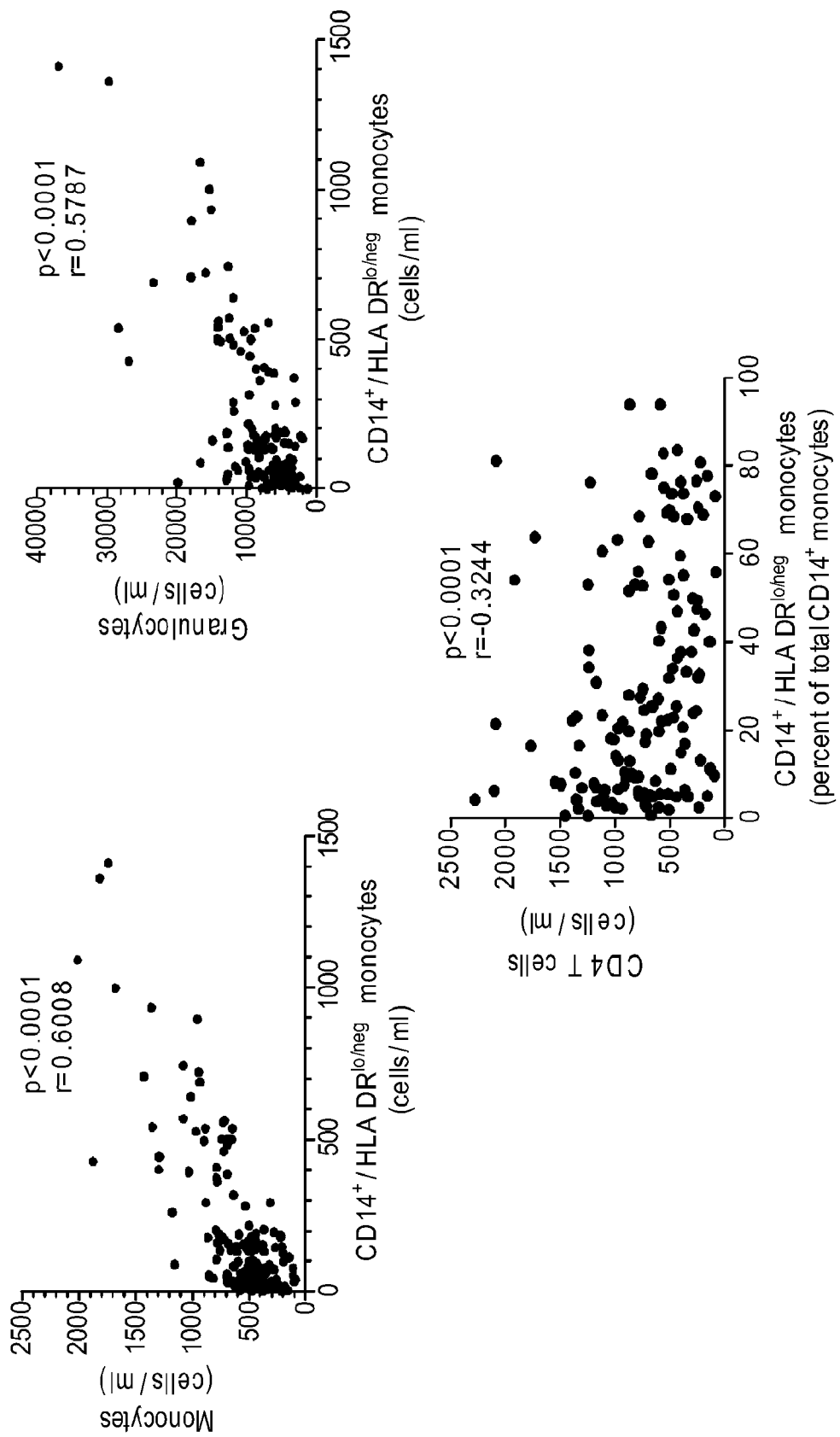

Two markers clustering largely to themselves were the $CTLA4^+$ T cells, and the $CD14^+HLA-DR^{lo/neg}$ phenotype. $CD14^+HLA-DR^{lo/neg}$ monocytes were identified as a predictor of poor prognosis and powerful mediators of immune suppression in GBM (Gustafson et al., Neuro. Oncol., 12:631 (2010)), NHL (Lin et al., Blood, 117:872 (2011)), chronic lymphocytic leukemia (CLL) (Gustafson et al., Br. J. Haematol., 156:674 (2012)), and RCC. This phenotype had one of the largest degrees of change in both relative and absolute terms in the analysis provided herein (FIG. 4 and Table 6). To investigate if this segregation could identify interesting correlations within the immune system, the complete cohort of patients and HV were used to perform correlation analyses with two closely related markers and one marker segregating at a distant to the $CD14^+HLA-DR^{lo/neg}$ phenotype. $CD14^+HLA-DR^{lo/neg}$ monocyte cell counts positively correlated with total monocyte and granulocyte counts, markers that closely segregated to the $CD14^+HLA-DR^{lo/neg}$ (FIG. 8B). In earlier analyses, $CD4^+$ T cell counts were inversely correlated to the percentage of $CD14^+HLA-DR^{lo/neg}$ monocytes (of total CD14+ monocytes) in GBM patients. Here, in a larger cohort of subjects including both volunteers and cancer patients, $CD4^+$ cells segregated distally from the $CD14^+HLA-DR^{lo/neg}$ phenotype and were inversely correlated to the percentage of $CD14^+HLA-DR^{lo/neg}$ monocytes (p<0.001; Spearman r=−0.3244). The data herein suggested certain markers such as $CD14^+HLA-DR^{lo/neg}$ monocytes may be largely independently regulated and are an important component of the leukocyte population key to the characterization of the overall status of the immune system. It also identified key inverted relationships that might lead to improved description of the immune system with seemingly unrelated immune phenotypes.

TABLE 6

Overall Survival Multivariate Cox Models in Cancer Patients.

| Phenotype (cells/µL) | P value |
|---|---|
| Lymphocytes | 0.2382 |
| Granulocytes | 0.0611 |
| Monocytes | 0.0563 |
| CD4 | 0.2206 |

TABLE 6-continued

Overall Survival Multivariate Cox Models in Cancer Patients.

| Phenotype (cells/µL) | P value |
|---|---|
| CD8 | 0.8504 |
| Regulatory T cells | 0.9381 |
| $CD14^+HLA-DR^{lo/neg}$ monocytes | 0.0348 |
| $CD86^+$ monocytes | 0.2405 |
| B cells | 0.9646 |
| NK cells | 0.9071 |

Figure 8C:
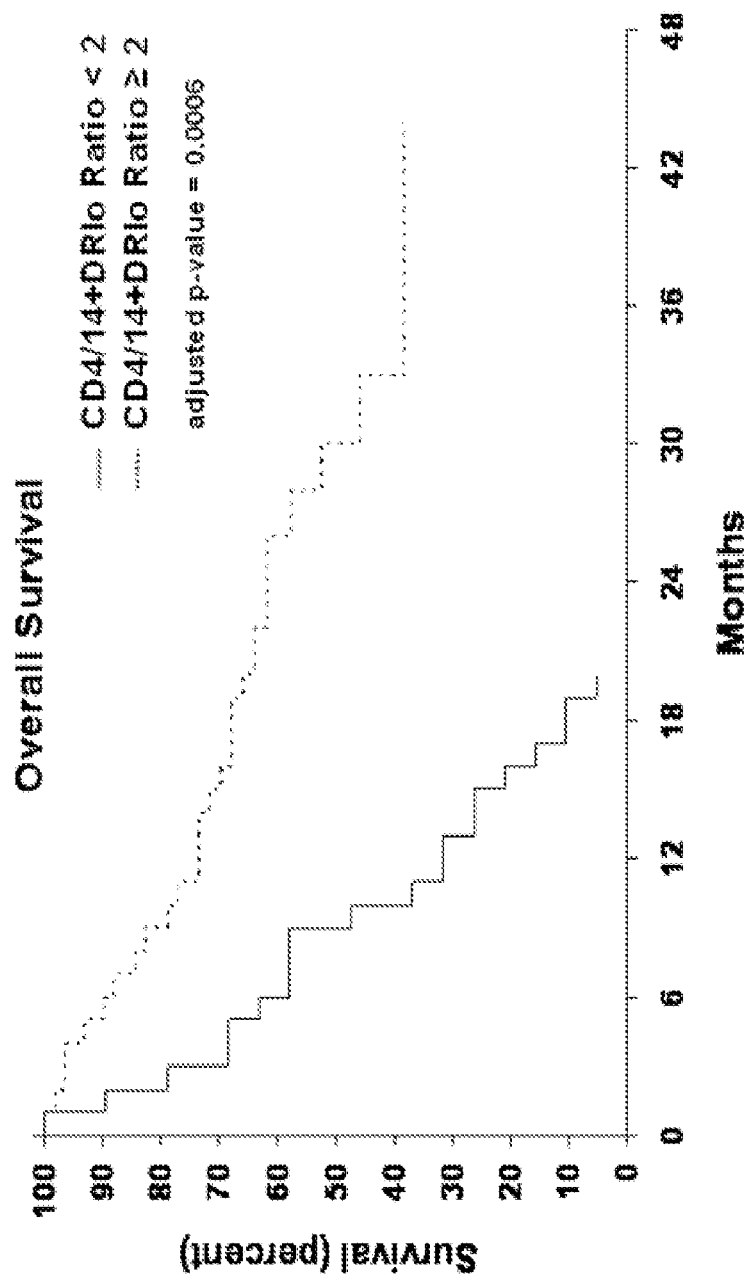

The $CD4^+/CD14^+HLA-DR^{lo/neg}$ Ratio is a Prognostic Biomarker in Cancer Patients The inverted relationship between $CD14^+HLA-DR^{lo/neg}$ and $CD4^+$ cells identified above was chosen to determine if selected but disparate informative markers could describe immune status. Analysis of the individual markers did not identify a survival difference although lymphocytes counts have proven to be useful prognostic markers in some cancer populations (Porrata et al., Biology of Blood & Marrow Transplantation, 14:807 (2008); and Ege et al., British Journal of Haematology, 141:792 (2008)). To describe the contribution of both variables, the ratio of the number of $CD4^+$ T cells to the number of $CD14^+HLA-DR^{lo/neg}$ monocytes (cells/µL) was calculated. The 40 healthy volunteers had a mean $CD4^+/CD14^+HLA-DR^{lo/neg}$ ratio of 39.8 (median 22.5) with a minimum of 3.9. The GBM, NHL, and RCC patients were subgrouped into those with high or low ratio, with a cut-point ratio of 2.0. The overall survival of GBM, NHL, and RCC patients with high and low ratio was analyzed using multivariate analysis to control for age and disease type. The median overall survival for patients with a ratio above 2.0 was 30 months (n=68) compared to 9 months for patients with a low ratio (n=39; p=0.006 by multivariate analysis) (FIG. 8C). These results demonstrate that this ratio is a strong predictive biomarker for risk stratification and prognosis.

This document provides methods and materials to describe comprehensively the immune system based on whole blood flow cytometry, determining the number of cells/µL for the major leukocyte components, and hierarchical clustering. Bioinformatics analysis was used to cluster individuals into immune profiles. The power of bioinformatics to cluster by similarity was related to the number of samples included in the analysis, the disease stratification, and how consistent all members within a profile are. The technical approach used (e.g., whole blood flow cytometry with cell quantitation) combined with a consensus antibody and gating strategy can be used to establish a comprehensive analysis of peripheral blood immunity with thousands of patients and healthy volunteers to extract relationships between immunity and disease.

The results provided herein involved (1) direct staining of fresh un-manipulated whole blood, (2) the use of an unbiased approach looking at multiple immune markers, (3) reporting cell populations as cell counts (cells/µL) to enumerate populations more accurately, and (4) a data set of healthy volunteers to determine the degree of change of immune markers. By combining these principles with gating strategies and patient health annotation, a large multi-institutional database can be established to provide a powerful resource for assessing human immunology.

Example 2—Immune System Profiles

The number of granulocytes, lymphocytes, monocytes, T cells, B cells, NK cells, $CD4^+$ lymphocytes, regulatory T cells, CD14+HLA-DR$^{lo/neg}$ monocytes, and CD86+ monocytes per μL of whole blood was determined for 40 healthy volunteers (HV), 97 cancer patients, and 23 patients with acute lung injury and used to identify the mean±1 standard deviation for immune system profiles 1, 2, 3, 4, and 5 (Table 7).

TABLE 7

Mean immune marker values in cells/μL of whole blood.

| Immune Marker | HV | Profile 1 | Profile 2 | Profile 3 | Profile 4 | Profile 5 |
|---|---|---|---|---|---|---|
| Granulocytes | 4679 ± 1610 | 6135 ± 2745 | 5508 ± 4911 | 12808 ± 7423 | 12402 ± 6469 | 6644 ± 3252 |
| Lymphocytes | 1722 ± 512 | 1579 ± 613 | 1948 ± 606 | 2242 ± 722 | 769 ± 250 | 645 ± 399 |
| Monocytes | 497 ± 148 | 533 ± 172 | 367 ± 105 | 1085 ± 375 | 784 ± 410 | 253 ± 151 |
| T cells | 1258 ± 387 | 1158 ± 470 | 1397 ± 522 | 1679 ± 638 | 563 ± 220 | 456 ± 375 |
| B cells | 243 ± 128 | 222 ± 166 | 225 ± 134 | 347 ± 209 | 109 ± 75 | 81 ± 87 |
| NK cells | 222 ± 102 | 200 ± 91 | 326 ± 285 | 215 ± 125 | 97 ± 72 | 107 ± 87 |
| CD4+ T cells | 921 ± 317 | 825 ± 350 | 885 ± 282 | 1201 ± 455 | 352 ± 156 | 381 ± 480 |
| Regulatory T cells | 28 ± 17 | 32 ± 23 | 30 ± 15 | 55 ± 32 | 13 ± 8 | 21 ± 24 |
| CD14+HLA-DR$^{lo/neg}$ monocytes | 51 ± 36 | 97 ± 88 | 10 ± 7 | 595 ± 312 | 426 ± 318 | 72 ± 58 |
| CD86+ monocytes | 455 ± 126 | 483 ± 157 | 336 ± 104 | 962 ± 351 | 613 ± 403 | 195 ± 155 |

In addition, the measured cell numbers were used to determine the mean ratio of each immune marker (i.e., cell type) in each profile compared to the healthy volunteer cohort±one standard deviation (Table 8).

TABLE 8

Mean immune marker ratio values.

| Immune Marker | HV | Profile 1 | Profile 2 | Profile 3 | Profile 4 | Profile 5 |
|---|---|---|---|---|---|---|
| Granulocytes | 1.00 ± 0.34 | 1.30 ± 0.59 | 1.23 ± 0.29 | 2.73 ± 1.59 | 2.65 ± 1.38 | 1.42 ± 0.70 |
| Lymphocytes | 1.00 ± 0.30 | 0.92 ± 0.35 | 1.10 ± 0.38 | 1.30 ± 0.42 | 0.45 ± 0.15 | 0.37 ± 0.23 |
| Monocytes | 1.00 ± 0.30 | 1.07 ± 0.35 | 0.75 ± 0.24 | 2.18 ± 0.76 | 1.58 ± 0.82 | 0.51 ± 0.30 |
| T cells | 1.00 ± 0.31 | 0.92 ± 0.37 | 1.08 ± 0.44 | 1.34 ± 0.51 | 0.45 ± 0.17 | 0.36 ± 0.30 |
| B cells | 1.00 ± 0.53 | 0.92 ± 0.68 | 0.91 ± 0.56 | 1.43 ± 0.86 | 0.45 ± 0.31 | 0.33 ± 0.36 |
| NK cells | 1.00 ± 0.46 | 0.91 ± 0.41 | 1.43 ± 1.31 | 0.97 ± 0.56 | 0.44 ± 0.32 | 0.49 ± 0.39 |
| CD4+ T cells | 1.00 ± 0.35 | 0.90 ± 0.38 | 0.91 ± 0.29 | 1.31 ± 0.49 | 0.38 ± 0.17 | 0.41 ± 0.52 |
| Regulatory T cells | 1.00 ± 0.58 | 1.13 ± 0.84 | 1.16 ± 0.51 | 1.96 ± 1.14 | 0.45 ± 0.28 | 0.74 ± 0.87 |
| CD14+HLA-DR$^{lo/neg}$ monocytes | 1.00 ± 0.73 | 1.89 ± 1.73 | 0.25 ± 0.19 | 11.66 ± 6.13 | 8.35 ± 6.23 | 1.42 ± 1.13 |
| CD86+ monocytes | 1.00 ± 0.28 | 1.06 ± 0.34 | 0.75 ± 0.26 | 2.11 ± 0.77 | 1.35 ± 0.89 | 0.43 ± 0.34 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining the immune system profile of a human having glioblastoma and treating said human, wherein said method comprises:
   (a) performing flow cytometry using whole blood obtained from a human to determine the numbers of CD4+ lymphocytes, CD8+ lymphocytes, regulatory T cells, B cells, NK cells, granulocytes, CD14+HLA-DR$^{lo/neg}$ monocytes, and CD86+ monocytes per unit volume of said whole blood,
   (b) obtaining a database comprising the numbers of CD4+ lymphocytes, CD8- lymphocytes, regulatory T cells, B cells, NK cells, granulocytes, CD14+HLA-DR$^{lo/neg}$ monocytes, and CD86+ monocytes per unit volume present within a population of healthy humans and a population of humans with a medical condition having a known outcome for said medical condition, wherein each member of said population of healthy humans and said population of humans with said medical condition is assigned to an immune system profile within said database using hierarchical clustering of said numbers of CD4+ lymphocytes, CD8+ lymphocytes, regulatory T cells, B cells, NK cells, granulocytes, CD14+HLA-DR$^{lo/neg}$ monocytes, and CD86+ monocytes per unit volume for said each member,
   (c) comparing said numbers of CD4+ lymphocytes, CD8+ lymphocytes, regulatory T cells, B cells, NK cells, granulocytes, CD14+HLA-DR$^{lo/neg}$ monocytes, and CD86+ monocytes per unit volume of said whole blood to information within said database,
   (d) classifying said human as having an immune system profile 1 or 2 if whole blood obtained from said human comprises (i) from about 3000 to about 9000 granulocytes, from about 950 to about 2500 lymphocytes, from about 350 to about 750 monocytes, from about 650 to about 1750 T cells, from about 50 to about 400 B cells, from about 100 to about 300 NK cells, from about 500 to about 1175 CD4+ lymphocytes, from about 5 to about 55 regulatory T cells, from about 10 to about 185 CD14+HLA-DR$^{lo/neg}$ monocytes, and from about 325 to about 650 CD86+ monocytes per μL or (ii) from about 550 to about 10500 granulocytes, from about 1300 to about 2600 lymphocytes, from about 250 to about 500 monocytes, from about 870 to about 1920 T cells, from about 90 to about 360 B cells, from about 40 to about 615 NK cells, from about 600 to about 1200 CD4$^+$ lymphocytes, from about 15 to about 45 regulatory T cells, from about 3 to about 17 CD14$^+$HLA-DR$^{lo/neg}$ monocytes, and from about 230 to about 440 CD86$^+$ monocytes per μL, and (e) administering surgery, radiation, or temazolimide to said human having said profile 1 or 2.

2. The method of claim 1, wherein said human is classified as having immune system profile 1.

3. The method of claim 1, wherein said whole blood is a fresh, un-manipulated whole blood sample obtained from said human.

* * * * *

UNITED STATES PATENT AND TRADEMARK OFFICE
CERTIFICATE OF CORRECTION

PATENT NO. : 9,970,936 B2
APPLICATION NO. : 14/442465
DATED : May 15, 2018
INVENTOR(S) : Michael P. Gustafson and Allan B. Dietz Page 1 of 1

It is certified that error appears in the above-identified patent and that said Letters Patent is hereby corrected as shown below:

In the Specification

Column 1, Line 9, delete "having and" and insert -- having an --, therefor.

In the Claims

Column 21, Line 66, Claim 1, delete "CD8-" and insert -- CD8+ --, therefor.

Column 22, Line 54, Claim 1, after "2" insert -- , --.

Column 23, Line 6, Claim 1, delete "temazolimide" and insert -- temozolomide --, therefor.

Signed and Sealed this
Thirtieth Day of July, 2019

Andrei Iancu
*Director of the United States Patent and Trademark Office*